(12) United States Patent
Yang et al.

(10) Patent No.: US 9,840,583 B2
(45) Date of Patent: Dec. 12, 2017

(54) FLUORESCENT POLYMERS AND APPLICATIONS THEREOF

(71) Applicants: Board of Regents, The University of Texas System, Austin, TX (US); The Penn State Research Foundation, University Park, PA (US)

(72) Inventors: Jian Yang, State College, PA (US); Zhiwei Xie, State College, PA (US)

(73) Assignees: Board of Regents, The University of Texas System, Austin, TX (US); The Penn State Research Foundation, University Park, PA (US)

( * ) Notice: Subject to any disclaimer, the term of this patent is extended or adjusted under 35 U.S.C. 154(b) by 0 days.

(21) Appl. No.: 14/903,181

(22) PCT Filed: Jul. 8, 2014

(86) PCT No.: PCT/US2014/045664
§ 371 (c)(1),
(2) Date: Jan. 6, 2016

(87) PCT Pub. No.: WO2015/006271
PCT Pub. Date: Jan. 15, 2015

(65) Prior Publication Data
US 2016/0137776 A1    May 19, 2016

Related U.S. Application Data

(60) Provisional application No. 61/843,958, filed on Jul. 9, 2013, provisional application No. 61/856,145, filed on Jul. 19, 2013.

(51) Int. Cl.
| | |
|---|---|
| *A61K 9/107* | (2006.01) |
| *C08G 63/91* | (2006.01) |
| *C08G 63/685* | (2006.01) |
| *A61K 47/34* | (2017.01) |

(52) U.S. Cl.
CPC ............ *C08G 63/914* (2013.01); *A61K 9/107* (2013.01); *C08G 63/6854* (2013.01); *A61K 9/1075* (2013.01); *A61K 47/34* (2013.01)

(58) Field of Classification Search
CPC ... A61K 9/107; C08G 63/6854; C08G 63/914
See application file for complete search history.

(56) References Cited

U.S. PATENT DOCUMENTS

| | | | |
|---|---|---|---|
| 2003/0219828 A1* | 11/2003 | Singh | ............... C08F 8/00 435/7.1 |
| 2004/0253203 A1 | 12/2004 | Hossainy | |
| 2007/0134332 A1 | 6/2007 | Turnell | |
| 2011/0183435 A1* | 7/2011 | Yang | ............... A61L 27/18 436/501 |

FOREIGN PATENT DOCUMENTS

| | | |
|---|---|---|
| EP | 0323267 | 7/1989 |
| WO | WO 2009155450 | 12/2009 |

OTHER PUBLICATIONS

Williams et al., Analyst 1983, 108, 1067.
Licciardi et al., Int. J. Pharm. 2010, 396, 219.
PCT/US2014/045664, Jul. 8, 2014 (Filing Date), WO 2015/006271 A1.
U.S. Appl. No. 61/856,145, filed Jul. 19, 2013.
U.S. Appl. No. 61/843,958, filed Jul. 9, 2013.
PCT International Search Report and Written Opinion for dated Jul. 10, 2014 for PCT/US2014/045664.

* cited by examiner

*Primary Examiner* — Kyle Purdy
(74) *Attorney, Agent, or Firm* — McCarter & English, LLP

(57) ABSTRACT

In one aspect, block copolymers are described herein. A block copolymer described herein, in some embodiments, comprises a first block comprising a polymer or oligomer formed from the reaction product of (i) a polycarboxylic acid or a polycarboxylic acid equivalent, (ii) a polyol, and (iii) an amino acid; and a second block comprising a polymer or oligomer that differs from the polymer or oligomer of the first block. In some cases, the polycarboxylic acid or polycarboxylic acid equivalent comprises citric acid, a citrate, or an ester of citric acid. The polyol can comprise an α,ω-n-alkane diol, poly(ethylene glycol), or poly(propylene glycol). In some embodiments, the amino acid forms a pendant group of the polymer or oligomer of the first block and/or forms a luminescent 6-membered ring with the polycarboxylic acid or polycarboxylic acid equivalent. The second block of a block copolymer described herein, in some embodiments, comprises a polylactone.

3 Claims, 19 Drawing Sheets

FIG. 1
Step 1
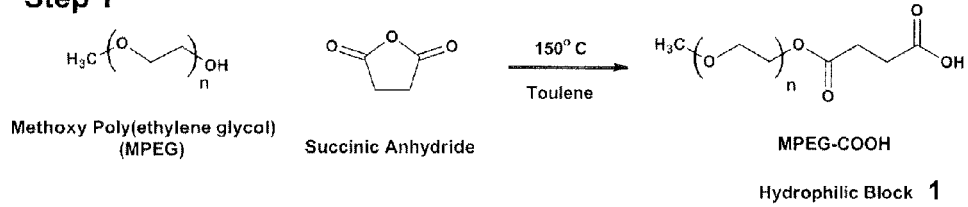
Step 2
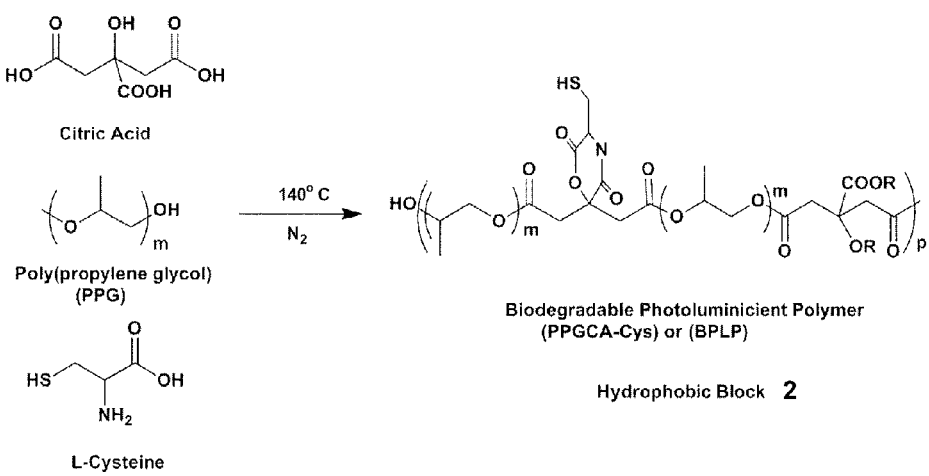
Step 3
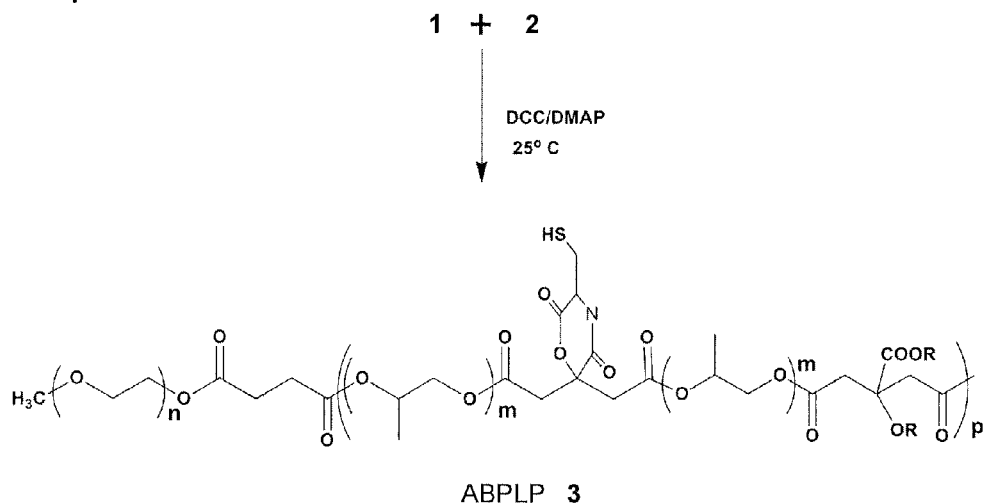

Amphiphilic Biodegradable Photoluminescent Polymer
(ABPLP)

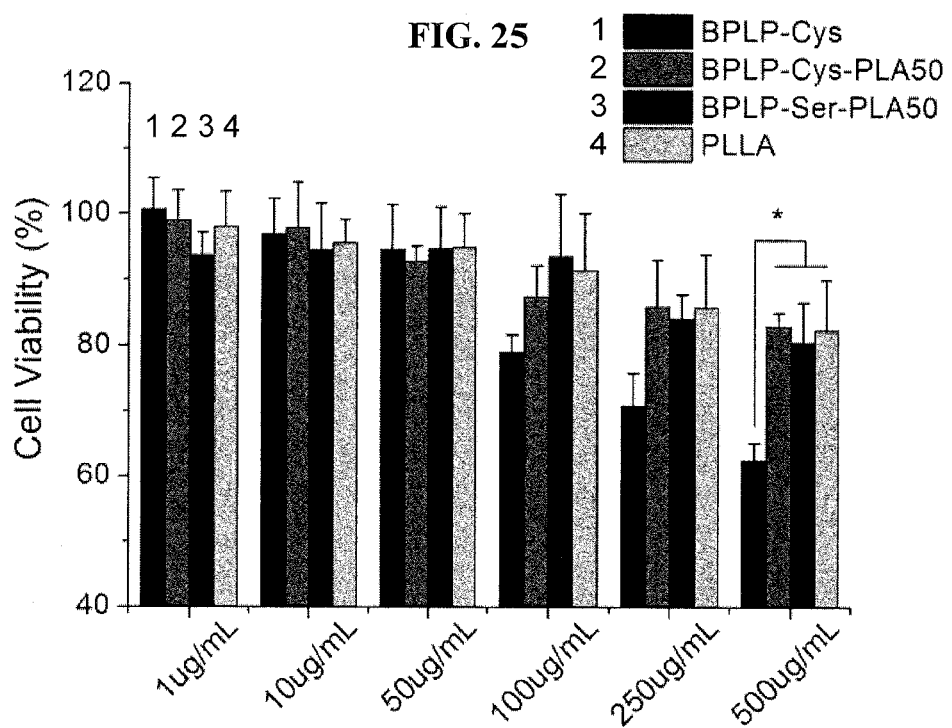
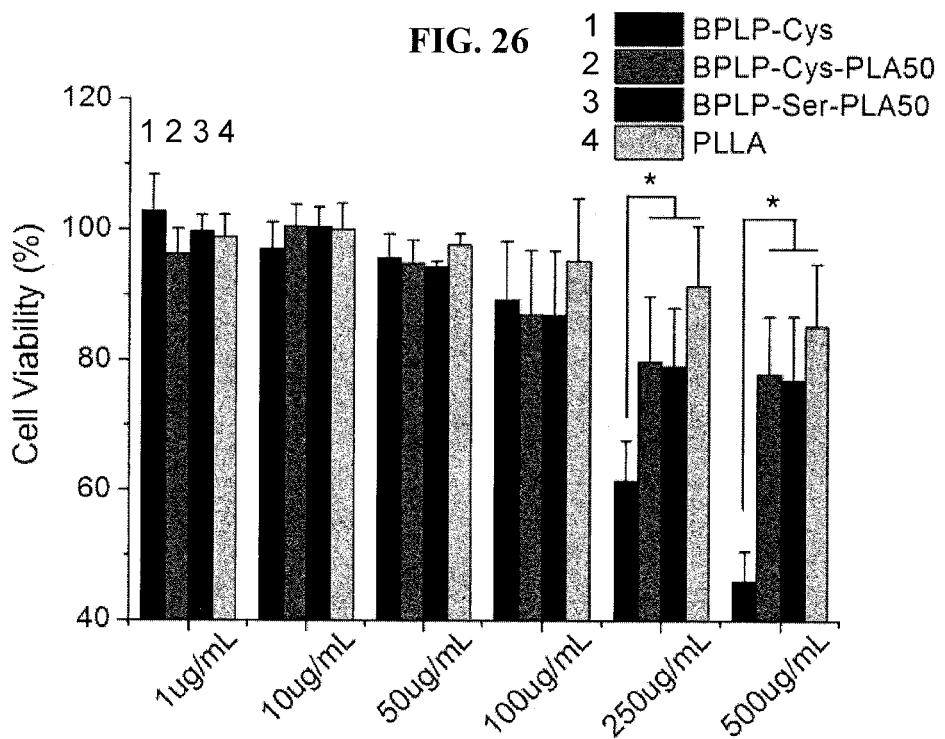

FLUORESCENT POLYMERS AND APPLICATIONS THEREOF

CROSS REFERENCE TO RELATED APPLICATIONS

This application claims priority pursuant to 35 U.S.C. §119 to U.S. Provisional Patent Application Ser. No. 61/843,958, filed on Jul. 9, 2013, and to U.S. Provisional Patent Application Ser. No. 61/856,145, filed on Jul. 19, 2013, each of which is hereby incorporated by reference in its entirety.

STATEMENT REGARDING FEDERALLY SPONSORED RESEARCH

This invention was made with government support under Grant No. DMR1313553, awarded by the National Science Foundation and under Grant No. EB012575, awarded by the National Institutes of Health. The Government has certain rights in the invention.

FIELD

This invention relates to fluorescent polymers and, in particular, to fluorescent block copolymers and structures formed from fluorescent block copolymers.

BACKGROUND

Polymers can be used for various biomedical and/or bioengineering applications. For example, polymers that are capable of self-assembling into thermodynamically stable micelles have become increasingly important in pharmaceutical and medical applications. In aqueous solution, micelles typically have a structure comprising a hydrophobic core or "tail" section at the interior of the micelle and a hydrophilic corona or "head" section at the exterior of the micelle in contact with the solvent. The hydrophobic core can house hydrophobic drugs, and the hydrophilic corona can function as a steric barrier to prevent micelle aggregation, ensuring micelle solubility in an aqueous environment.

In addition, fluorescent micelles have gained significant attention in recent years for so-called "theranostic" (therapeutic plus diagnostic) applications. Existing strategies to provide fluorescent properties to micelles are typically centered on conjugating or encapsulating fluorescent organic dyes (such as rhodamines, cyanines, or fluorescein), quantum dots, or gold nanoparticles on or within the micelles. However, conjugation or encapsulation of these materials often results in low fluorophore-to-micelle ratios, increased micelle size, inferior photo-bleaching resistance, and/or significant cytotoxicity. Further, premature leakage of some fluorophores into surrounding tissues can interfere with the detection of samples of interest. Therefore, there is a need for improved fluorescent micelles and improved methods of making and using fluorescent micelles.

Similarly, there is also a need for improved fluorescent polymers that may or may not form micelles. For example, some polylactones have been approved by the United States Food and Drug Administration (FDA) for use in biomedical implants such as orthopedic fixation devices and tissue grafts. In addition, synthetic polylactones can be biodegradable. However, the structure of some existing polylactones does not provide self-reporting of the degradation of biomedical implants formed from the polylactones. The resulting lack of in vivo quantitative data regarding degradation and variation in biological activity has significantly hindered the development of improved implants for use in vivo. Thus, there is a need for polymers that can enable in situ, real-time monitoring of the degradation of an implant without open surgery or animal sacrifice. Similarly, some existing polylactones do not provide theranostic capabilities. Specifically, some polylactones cannot be used for both imaging and therapeutics without the conjugation and/or encapsulation of various imaging agents by the polylactones. Such conjugation and/or encapsulation can result in dramatically increased particle size, additional cost or complexity, and/or a higher risk of adverse biological reactions to the theranostic agent.

SUMMARY

In one aspect, polymers are described herein which, in some embodiments, may provide one or more advantages over some previous polymers. For example, in some cases, a block copolymer described herein can be amphiphilic and can self-assemble into a nanoscale micelle, such as a micelle having a hydrophobic core and a hydrophilic corona. Further, in some instances, a block copolymer described herein can be luminescent or fluorescent and/or biodegradable, facilitating its use in a variety of biological applications, including imaging applications, therapeutic applications, and/or theranostic applications.

Further, in some embodiments, a block copolymer described herein can comprise one or more polylactone blocks and can be used in any biomedical or non-biomedical application for which a polylactone may be used. For example, such a block copolymer described herein can be used as a drug-eluting stent or other drug delivery device, a disposable medical device, a medical implant, a tissue engineering scaffold, and/or a molecular targeting carrier. Additionally, in some cases, such a block copolymer can be luminescent or fluorescent, including without the use of any additional dye or other luminescent or fluorescent material, such as a semiconductor nanocrystal or quantum dot. Moreover, a block copolymer described herein, in some embodiments, can be formed from and subsequently biodegrade into only non-toxic materials and/or materials approved by the FDA for use in biomedical devices or other biomedical applications. Further, in some cases, a nanoparticle or other structure formed from a block copolymer described herein can be used for in vivo fluorescence imaging and/or theranostic cancer drug delivery, targeting, and diagnosis. Moreover, in some instances, medical devices or implants comprising or formed from a block copolymer described herein can enable in situ fluorescence monitoring of implant degradation and/or in vivo tissue regeneration without the need to sacrifice an animal model and/or carry out histological analyses. Block copolymers described herein may also be used in additional tissue engineering, wound healing, medical implant, diagnostic agent, drug delivery, biosensing, cosmetics, personal care, packaging, fluorescence labeling, surgical material, construction, painting, and/or coating applications.

In some embodiments, a block copolymer described herein comprises a first block comprising a polymer or oligomer formed from the reaction product of (i) a polycarboxylic acid or a polycarboxylic acid equivalent, (ii) a polyol, and (iii) an amino acid; and a second block comprising a polymer or oligomer that differs from the polymer or oligomer of the first block. In some cases, the polycarboxylic acid or polycarboxylic acid equivalent of the first block comprises citric acid, a citrate, or an ester of citric acid. Further, in some instances, the polyol of the first block comprises an α,ω-n-alkane diol, a poly(ethylene glycol), or a poly(propylene glycol). Additionally, in some embodiments, the amino acid used to form the polymer or oligomer of the first block of a block copolymer described herein comprises an alpha-amino acid. Moreover, in some cases, the amino acid forms a pendant group of the polymer or oligomer of the first block. Further, in some instances, the amino acid forms a 6-membered ring with the polycarboxylic acid or polycarboxylic acid equivalent. In some such cases, the 6-membered ring can be luminescent or fluorescent, thereby providing luminescence or fluorescence to the polymer or oligomer. Further, a first block of a block copolymer described herein can be hydrophobic or hydrophilic.

Additionally, in some embodiments, a second block of a block copolymer described herein is hydrophilic. In some cases, for instance, a hydrophilic second block comprises or is formed from a poly(ethylene glycol) (PEG) or another hydrophilic polymer or oligomer. Further, in some embodiments, a second block of a block copolymer described herein is formed from a hydrophilic polymer or oligomer comprising at least one carboxylic acid terminus. In some cases, the polymer or oligomer of a second block described herein comprises or is formed from a polylactone such as a polylactide (PLA), a polyglycolide, a polycaprolactone, or a mixture or copolymer of one or more of the foregoing.

Further, a block copolymer described herein, in some embodiments, is amphiphilic. In some cases, such a block copolymer comprises a plurality of hydrophilic blocks connected by one or more hydrophobic blocks.

In another aspect, secondary structures of block copolymers are described herein. In some cases, such a secondary structure comprises a micelle or nanoparticle. In other instances, a secondary structure comprises a film or a graft or scaffold. As described further hereinbelow, such secondary structures can be formed from any block copolymer described hereinabove. For example, in some embodiments, a micelle is formed from an amphiphilic block copolymer described hereinabove. In some cases, such a micelle can be formed from an amphiphilic polymer comprising at least one hydrophilic block comprising a hydrophilic polymer or oligomer; and at least one hydrophobic block comprising a hydrophobic polymer or oligomer, wherein the hydrophilic polymer or oligomer and/or the hydrophobic polymer or oligomer is formed from the reaction product of (i) a polycarboxylic acid or a polycarboxylic acid equivalent, (ii) a polyol, and (iii) an amino acid. Further, in some embodiments, the hydrophilic block and the hydrophobic block are bonded together through an ester linkage. Additionally, a micelle described herein, in some instances, has a hydrophobic core and a hydrophilic corona. In some cases, such a micelle further comprises a drug disposed in the hydrophobic core of the micelle. Moreover, a micelle described herein can be a luminescent or fluorescent micelle.

Secondary structures of block copolymers described herein can also comprise films, grafts or scaffolds, and/or nanoparticles. In some embodiments, a film, scaffold, and/or nanoparticle described herein comprises a dried and/or crosslinked block copolymer described hereinabove. In some cases, a block copolymer is crosslinked through one or more side chains or pendant groups of the block copolymer, such as through one or more ethyleneically unsaturated moieties pendant to the block copolymer. A block copolymer may also be crosslinked through a pendant carboxyl, carboxylate, or hydroxyl moiety. Moreover, in some embodiments, a structure described herein forms an article or medical device such as an orthopedic fixation device, a tissue graft, a fiber, or a suture.

In another aspect, methods of imaging a biological compartment are described herein. In some embodiments, a method of imaging comprises disposing a structure described hereinabove in a biological compartment and using the structure to image the compartment. For example, in some cases, a method of imaging comprises disposing a micelle formed from an amphiphilic polymer in a biological compartment; irradiating the micelle with electromagnetic radiation at least partially overlapping the absorption profile of the amphiphilic polymer to induce fluorescence from the amphiphilic polymer; and detecting the fluorescence with a detector, wherein the amphiphilic polymer comprises a block copolymer described herein.

In still another aspect, methods of treating diseased tissue are described herein. In some embodiments, a method of treating diseased tissue comprises disposing a structure described hereinabove in a biological compartment. In some cases, the structure comprises a drug or other therapeutic composition. For example, in some embodiments, a method of treating diseased tissue comprises (a) disposing a micelle described hereinabove in a biological compartment, the micelle comprising a hydrophobic core, a hydrophilic corona, and a drug disposed in the hydrophobic core; and (b) releasing the drug into the biological compartment. Additionally, in some embodiments, a method of treating diseased tissue described herein can further comprise imaging the diseased tissue. For example, in some cases, a method described herein further comprises irradiating the micelle with electromagnetic radiation at least partially overlapping the absorption profile of the amphiphilic polymer of the micelle to induce fluorescence or other luminescence from the amphiphilic polymer; and detecting the fluorescence or other luminescence with a detector. Therefore, in some embodiments, a micelle or other secondary structure described herein can be used for theranostic applications as well as imaging and/or therapeutic applications.

These and other embodiments are described in greater detail in the detailed description which follows.

BRIEF DESCRIPTION OF THE FIGURES

FIG. 1 illustrates a reaction scheme for making block copolymers according to some embodiments described herein.

FIG. 25 and FIG. 26 each illustrates in vitro properties of block copolymers according to some embodiments described herein.

DETAILED DESCRIPTION

Figure 2:
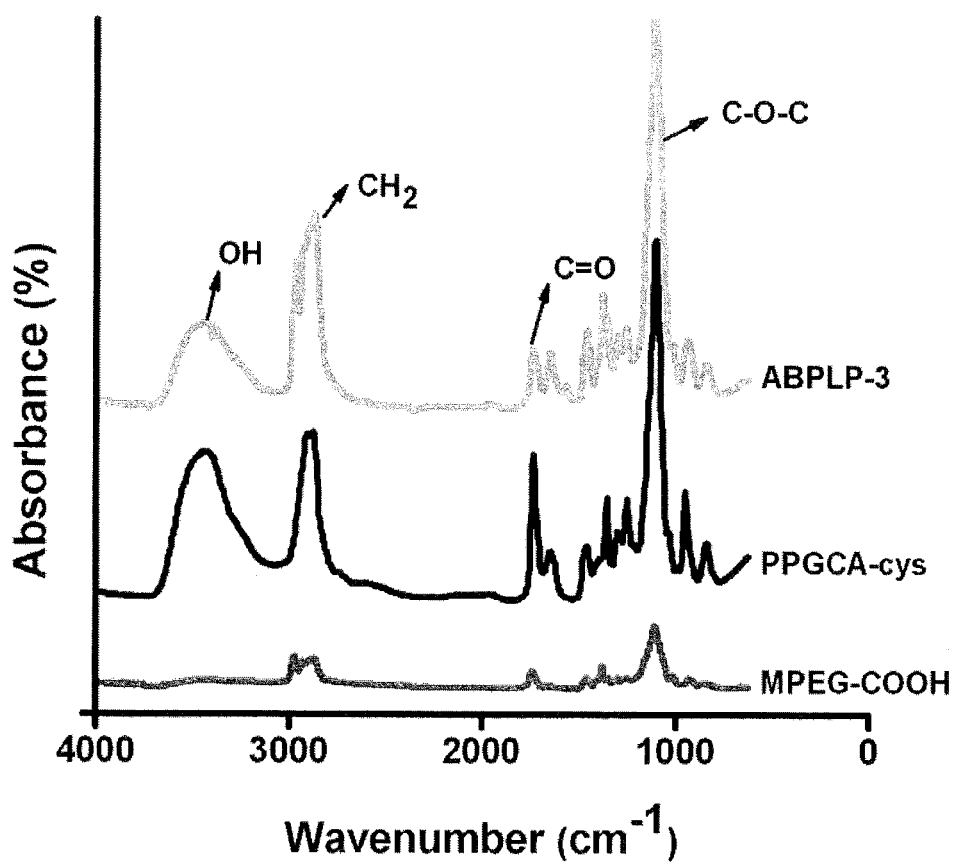
FIG. 2 illustrates Fourier Transform Infrared (FTIR) spectra of components of a block copolymer according to one embodiment described herein.

Embodiments described herein can be understood more readily by reference to the following detailed description, examples, and figures. Elements, apparatus, and methods described herein, however, are not limited to the specific embodiments presented in the detailed description, examples, and figures. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

I. Block Copolymers

In one aspect, block copolymers are described herein. In some embodiments, a block copolymer described herein comprises a first block comprising a polymer or oligomer formed from the reaction product of (i) a polycarboxylic acid or a polycarboxylic acid equivalent, (ii) a polyol, and (iii) an amino acid; and a second block comprising a polymer or oligomer that differs from the polymer or oligomer of the first block. Further, in some cases, a block copolymer described herein comprises more than one first block and/or more than one second block. In some embodiments, for instance, a block copolymer comprises a plurality of second blocks connected by one or more first blocks. In some cases wherein a plurality of first blocks and second blocks are present, the first blocks and second blocks can be arranged in an alternating manner to provide an A-B-A-B-type block copolymer. Other configurations are also possible, such as an A-B-A configuration. Moreover, in some embodiments, the blocks of a block copolymer described herein can be arranged to provide a block copolymer that is amphiphilic.

Turning now to components of block copolymers described herein, the polycarboxylic acid or polycarboxylic acid equivalent used to form the polymer or oligomer of the first block can comprise any chemical species not inconsistent with the objectives of the present disclosure. Further, a polycarboxylic acid "equivalent," for reference purposes herein, comprises a chemical species such as an acid anhydride, acid chloride, or a carboxylate or methyl or ethyl ester of a polycarboxylic acid that forms the same condensation reaction product as the corresponding polycarboxylic acid forms when reacted with an alcohol such as a diol (except the small molecule produced by the reaction, such as water or methanol, may differ). A polycarboxylic acid, in some embodiments, comprises a dicarboxylic acid or a tricarboxylic acid.

Further, in some cases, a polycarboxylic acid or polycarboxylic acid equivalent described herein comprises one or more additional moieties operable to form a linkage with an amino acid described herein. For example, in some instances, a polycarboxylic acid or polycarboxylic acid equivalent comprises a hydroxyl moiety. Moreover, in some implementations, the additional moiety, such as an additional hydroxyl moiety, is geminal to a carboxylic acid functional group of the polycarboxylic acid or polycarboxylic acid equivalent. In some embodiments, a polycarboxylic acid or polycarboxylic acid equivalent comprises citric acid, a citrate, or an ester of citric acid, such as triethyl citrate or another methyl or ethyl ester of citric acid.

Moreover, a polycarboxylic acid or functional equivalent thereof can be saturated or unsaturated. For example, in some instances, a polycarboxylic acid or polycarboxylic acid equivalent comprises maleic acid, maleic anhydride, tricarballylic acid, succinic acid, fumaric acid, or fumaryl chloride. A vinyl- or allyl-containing polycarboxylic acid or polycarboxylic acid equivalent may also be used, such as allylmalonic acid, allylmalonic chloride, itaconic acid, or itaconic chloride. Further, in some cases, a polycarboxylic acid or polycarboxylic acid equivalent can be partially replaced with an olefin-containing monomer that may or may not be a polycarboxylic acid. In some embodiments, for instance, an olefin-containing monomer comprises an unsaturated polyol such as a vinyl-containing diol.

Any polyol not inconsistent with the objectives of the present disclosure may be used to form a polymer or oligomer of a first block of a block copolymer described herein. In some cases, for instance, a polyol comprises a diol. A diol, in some embodiments, is a macrodiol. A "macrodiol," for reference purposes herein, comprises a polymer or oligomer comprising terminal hydroxyl groups. For example, in some embodiments, a macrodiol can be a poly(lactic acid) or another hydrophobic polymer or oligomer functionalized or derivatized to be a diol. Further, in some instances, a polyol comprises a poly(ethylene glycol) (PEG) or polypropylene glycol) (PPG). Any PEG or PPG not inconsistent with the objectives of the present disclosure may be used. In some embodiments, for instance, a PEG or PPG has a weight average molecular weight between about 100 and about 5000 or between about 200 and about 1000.

In other embodiments, a polyol is a small molecule diol such as a diol comprising from about 8 to about 30 carbon atoms (which can also be referred to as a C8-C30 diol). A C8-C30 diol can be linear or branched, aliphatic or aromatic. Non-limiting examples of polyols suitable for use in some embodiments described herein include C2-C20, C2-C12, or C2-C6 aliphatic alkane diols, including α,ω-n-alkane diols, or α,ω-alkene diols. For instance, in some cases, a polyol comprises 1,4-butanediol, 1,6-hexanediol, 1,8-octanediol, 1,10-decanediol, 1,12-dodacanediol, 1,16-hexadecanediol, or 1,20-icosanediol. Branched α,ω-alkane diols or α,ω-alkene diols can also be used. Additionally, a polyol can also be an aromatic diol. Further, in some cases, a polyol described herein comprises a triol, tetraol or higher polyol.

An amino acid used to form the polymer or oligomer of a first block described herein can comprise any amino acid not inconsistent with the objectives of the present disclosure. In some embodiments, an amino acid comprises an alpha-amino acid. Further, an alpha-amino acid of a polymer or oligomer described herein, in some cases, comprises an L-amino acid, a D-amino acid, or a D,L-amino acid. In some cases, an amino acid comprises alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, or a combination thereof. Moreover, in some instances, an alpha-amino acid comprises an alkyl ester amino acid, an aryl ester amino acid, or an alkyl-substituted alpha-amino acid, such as a methyl-substituted amino acid derived from any of the 22 "standard" or proteinogenic amino acids, such as S-benzyl-L-cysteine, S-phenyl-S-cysteine, tryptophan benzyl ester, S-methyl-cysteine, L-histidine methyl ester, phenylalanine methyl ester, L-tyrosine methyl ester, 1-methyl-L-histidine, 1-methyl-D-tryptophan, 1-methyl-L-tryptophan, or methyl serine. An amino acid may also be a non-naturally occurring amino acid or amino acid derivative. Further, in some cases, an amino acid comprises an amino acid dimer or trimer or a peptide, including but not limited to cystine, glycylglycine, anserine, carnosine, aspartame, arginylglycylaspartic acid (RGD), glutathione, or ophthalmic acid.

In addition, in some embodiments described herein, the amino acid forms a pendant group of the polymer or oligomer of the first block of the block copolymer. Such an amino acid pendant group can be bonded to the backbone of the polymer or oligomer in any manner not inconsistent with the objectives of the present disclosure. For example, in some cases, the amino acid is bonded to the backbone through an ester and/or amide bond between the amino acid and the polycarboxylic acid or polycarboxylic acid equivalent. Moreover, in some instances, the amino acid forms a 6-membered ring with the polycarboxylic acid or polycarboxylic acid equivalent. Not intending to be bound by theory, it is believed that the formation of a 6-membered ring described herein can provide luminescence such as fluorescence to the block copolymer, as described further hereinbelow. Thus, in some embodiments, the polymer or oligomer of a first block described herein can be a luminescent or fluorescent polymer or oligomer.

A luminescent or fluorescent polymer or oligomer described herein, in some instances, can exhibit a luminescence or fluorescence emission profile centered in the visible or near infrared (NIR) region of the electromagnetic spectrum. For example, in some embodiments, a luminescent or fluorescent polymer or oligomer described herein, in some instances, exhibits a luminescence or fluorescence emission profile centered at a wavelength between about 350 nm and about 750 nm, between about 390 nm and about 725 nm, between about 430 nm and about 650 nm, or between about 500 nm and about 700 nm. Moreover, in some implementations, a luminescent or fluorescent polymer or oligomer described herein resists photobleaching and/or has superior photobleaching characteristics compared to some other organic dyes.

Further, in addition to or instead of the polymers or oligomers described above, a first block of a block copolymer described herein can also comprise a polymer or oligomer formed from the reaction product of (i) a polycarboxylic acid or a polycarboxylic acid equivalent with (ii) a polyol, (iii) an amino acid, and (iv) an isocyanate such as a diisocyanate. An isocyanate, in some embodiments, comprises a monoisocyanate. In other instances, an isocyanate comprises a diisocyanate such as an alkane diisocyanate having four to twenty carbon atoms.

A reaction product described hereinabove, in some cases, is a condensation polymerization reaction product of the identified species. Thus, in some embodiments, at least two of the identified species are comonomers for the formation of a copolymer or cooligomer. In some such embodiments, the reaction product forms an alternating copolymer or a statistical copolymer of the comonomers. Additionally, as described further herein, species described hereinabove may also form pendant groups or side chains of a copolymer or cooligomer forming a first block of a block copolymer described herein.

In some embodiments, a polymer or oligomer of a first block of a block copolymer described herein is formed from one or more monomers of Formula (A), one or more monomers of Formula (B), (B') or (B"), and one or more monomers of Formula (E):

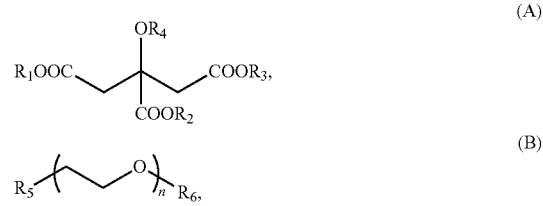

-continued

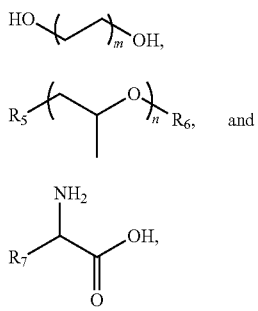

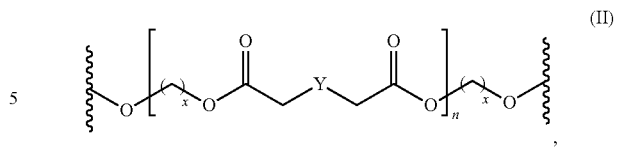

wherein each Y is independently selected from the group consisting of structures (a), (b), and (c):

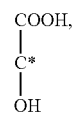

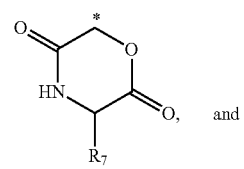

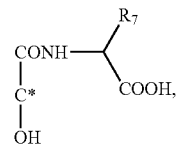

wherein R₁, R₂, and R₃ are independently —H, —CH₃, —CH₂CH₃, or M⁺;
R₄ is —H;
R₅ is —H, —OH, —OCH₃, —OCH₂CH₃, —CH₃, or —CH₂CH₃;
R₆ is —H, —CH₃, or —CH₂CH₃;
R₇ is a side chain or "R group" of an amino acid described above, such as one of the 22 "standard" or proteinogenic amino acids;
M⁺ is a cation such as Na⁺ or K⁺; and
n and m are independently integers ranging from 1 to 20.
In some cases, for example, R₇ is —CH₂SH (for E=cysteine) or —CH₂OH (for E=serine).
Further, in some embodiments, R₁, R₂, and R₃ are —H, R₅ is —OH, and R₆ is —H.

Moreover, the monomers of Formula (A), (B), (B'), (B") and (E) can be used in any ratio not inconsistent with the objectives of the present disclosure to form a polymer or oligomer. In addition, altering the ratios of monomers can, in some embodiments, alter the hydrophobicity, hydrophilicity, and/or other properties of the polymer or oligomer formed from the monomers. In some embodiments, the ratio of monomer (A) to monomer (B), (B'), or (B") is between about 1:10 and about 10:1 or between about 1:5 and about 5:1. In some cases, the ratio of monomer (A) to monomer (B), (B'), or (B") is between about 1:4 and about 4:1. In some instances, the ratio is about 1:1. Further, in some embodiments, the ratio of monomer (A) to monomer (E) is between about 1:10 and about 10:1.

In some embodiments, the polymer or oligomer of the first block has the structure of Formula (I):

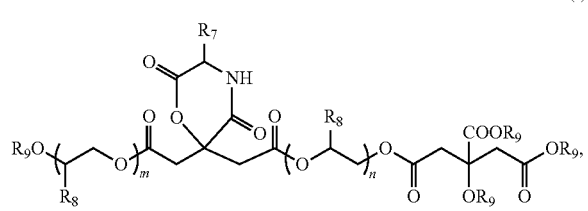

wherein R₇ is a side chain or "R group" of an amino acid described herein, such as one of the 22 standard amino acids;
each R₈ is independently —H or —CH₃;
each R₉ is independently —H or ∼∼∼;
∼∼∼ represents an additional chain of repeating units having the structure of Formula (I); and
m and n are independently integers ranging from 2 to 20.
In other cases, the polymer or oligomer of the first block has the structure of Formula (II):

wherein * represents the carbon atom that is the point of attachment to each —CH₂— group bound to Y;
each R₇ is independently a side chain or "R group" of an amino acid such as one of the 22 standard amino acids provided above;
each x is independently an integer from 2 to 12;
n is 2 to 12; and
at least one Y is structure (b).

The properties of a polymer or oligomer of a first block described herein, in some cases, can be selected based on the chemical identities and/or relative amounts of the monomers or reactants used to form the polymer or oligomer. In some embodiments, for example, the hydrophobicity, hydrophilicity, electromagnetic absorption and/or emission profile, brightness, luminescence quantum yield, and/or biodegradability of a polymer or oligomer can be selected based on monomers or reactants used to form the polymer or oligomer. The ability of a block copolymer to form secondary structures such as films and/or micelles can also be selected based on the choice of monomers or reactants used to form the polymer or oligomer of a first block of the block copolymer. In some cases, for instance, a polymer or oligomer described herein formed from a PPG or other relatively hydrophobic polyol can provide a relatively hydrophobic block. Alternatively, in other embodiments, a polymer or oligomer formed from a PEG or other relatively hydrophilic polyol can provide a relatively hydrophilic block. Thus, in some cases, a first block of a block copolymer described herein is a hydrophilic block. In other instances, a first block is a hydrophobic block.

In addition, a first block of a block copolymer described herein can have any molecular weight not inconsistent with the objectives of the present disclosure. In some embodiments, a first block has a weight average molecular weight of less than about 20,000 or less than about 15,000. In some embodiments, a first block has a weight average molecular weight of about 1000 to about 20,000, about 5000 to about 15,000, about 5000 to about 12,000, or about 10,000 to about 17,000. In some cases, a first block having a weight average molecular weight recited above may be a hydrophobic block. A first block described herein may also have a weight average molecular weight greater than about 15,000 or greater than about 20,000.

Further, one or more first blocks of a block copolymer described herein can be present in the block copolymer in any amount not inconsistent with the objectives of the present disclosure. In some embodiments, for instance, one or more first blocks are present in the block copolymer in an amount of about 5 weight percent to about 70 weight percent, based on the total weight of the block copolymer. In other embodiments, one or more first blocks are present in an amount of about 10 weight percent to about 50 weight percent or about 10 weight percent to about 30 weight percent.

The polymer or oligomer of a second block of a block copolymer described herein can comprise any polymer or oligomer not inconsistent with the objectives of the present disclosure. In some cases, the chemical identity and/or size of the polymer or oligomer of the second block is selected based on the chemical identity and/or size of the polymer or oligomer of the first block. For example, in some cases, a hydrophobic second block is selected in combination with a hydrophilic first block to provide an amphiphilic block copolymer. In other cases, a hydrophilic second block is used in combination with a hydrophobic first block. Additionally, in some embodiments, both the first block and the second block are hydrophobic. In other instances, both the first block and the second block are hydrophilic.

In some embodiments wherein the second block is hydrophilic, the polymer or oligomer of the second block comprises a hydrophilic polymer or oligomer. Any hydrophilic polymer or oligomer not inconsistent with the objectives of the present disclosure may be used. In some embodiments, for instance, the second block comprises or is formed from a polysaccharide such as a starch, cellulose, or chitin. In other cases, a hydrophilic second block comprises or is formed from a PEG. Any PEG not inconsistent with the objectives of the present disclosure may be used. In some embodiments, for instance, the PEG comprises an alkyl or alkoxy terminated PEG such as methoxy poly(ethylene glycol) (MPEG).

Further, in some embodiments, a second block of a block copolymer described herein is formed from a hydrophilic polymer or oligomer comprising at least one carboxylic acid terminus For example, in some cases, a second block is formed from a PEG, polysaccharide, or other hydrophilic polymer or oligomer derivatized or functionalized with a carboxylic acid. Such derivatization or functionalization can be carried out in any manner not inconsistent with the objectives of the present disclosure. For instance, in some embodiments, a hydrophilic polymer or oligomer comprising a hydroxyl group is reacted with an acid anhydride such as succinic anhydride to provide the corresponding carboxylic acid of the hydrophilic polymer or oligomer. Additionally, in some instances, a second block of a block copolymer described herein is formed from a hydrophilic polymer or oligomer comprising a carboxylic acid terminus and an alkyl or alkoxy terminus. A carboxylic acid terminus, in some instances, can facilitate the formation of an ester linkage of the polymer or oligomer with a polymer or oligomer of another block, such as a hydroxyl terminated polymer or oligomer of another block of the block copolymer.

Further, in some cases, a polymer or oligomer of a second block is chosen to provide a property or feature to a block copolymer in addition to or instead of hydrophobicity or hydrophilicity. For example, in some embodiments, a polymer or oligomer of a second block is biodegradable. A biodegradable polymer or oligomer, in some embodiments, degrades in vivo to non-toxic components which can be cleared from the body by ordinary biological processes. Such processes can include biologically assisted mechanisms, such as enzyme catalyzed reactions, or chemical mechanisms, such as hydrolysis. In some embodiments, a biodegradable material described herein completely or substantially completely degrades in vivo over the course of about 90 days or less, about 60 days or less, or about 30 days or less, where the extent of degradation is based on percent mass loss of the biodegradable material, and wherein complete degradation corresponds to 100% mass loss. Specifically, the mass loss is calculated by comparing the initial weight ($W_0$) of the material with the weight measured at a pre-determined time point ($W_t$) (such as 30 days), as shown in equation (1):

$$\text{Mass loss (\%)} = \frac{(W_0 - W_t)}{W_0} \times 100. \tag{1}$$

Moreover, in some embodiments, a polymer or oligomer described herein is biocompatible or cytocompatible. A biocompatible or cytocompatible polymer or oligomer, in some embodiments, is non-toxic and does not cause substantial tissue inflammation.

Further, in some instances, a polymer or oligomer of a second block is suitable for use in one or more tissue engineering or bioengineering applications. In some cases, the polymer or oligomer of a second block described herein comprises a polylactone. For example, in some embodiments, the polymer or oligomer of a second block comprises a polylactide (PLA) such as a poly-D,L-lactide, poly-D-lactide, or poly-L-lactide; a polyglycolide; or a polycaprolactone (PCL) such as poly-ε-caprolactone. Further, in some cases, the polymer or oligomer of a second block comprises a mixture or copolymer of one or more of the foregoing, such as poly(lactic-co-glycolic acid) (PLGA). Other polylactones may also be used. In general, a polylactone can comprise any polymer or oligomer that can be derived from lactone or cyclic ester monomer units, such as L-lactide, D-lactide, D,L-lactide, glycolide, and/or ε-caprolactone. Moreover, it is also possible, in some embodiments, to form a polymer or oligomer of the second block of a block copolymer described herein from one or more hydroxyalkanoates, carbonates, and/or anhydrides. For example, in some cases, a second block of a block copolymer described herein comprises or is formed from a polyhydroxyalkanoate (PHA).

In some cases, the polymer or oligomer of the second block of a block copolymer described herein has the structure of Formula (III), Formula (IV), or Formula (V):

(III)

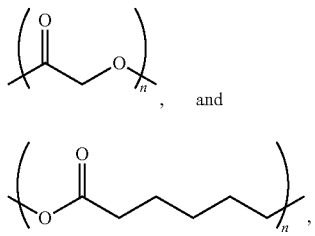
and (V)

wherein
n is 2 to 1000, 2 to 500, or 2 to 100.

A second block of a block copolymer described herein can have any molecular weight not inconsistent with the objectives of the present disclosure. In some embodiments, a second block has a weight average molecular weight of less than about 20,000 or less than about 15,000. In some embodiments, a second block has a weight average molecular weight of about 1000 to about 20,000, about 5000 to about 15,000, about 5000 to about 12,000, or about 10,000 to about 17,000. In some cases, a second block having a weight average molecular weight recited above may be a hydrophilic block. A second block described herein may also have a weight average molecular weight greater than about 15,000 or greater than about 20,000.

Moreover, one or more second blocks of a block copolymer described herein can be present in the block copolymer in any amount not inconsistent with the objectives of the present disclosure. In some embodiments, for instance, one or more second blocks are present in the block copolymer in an amount of about 5 weight percent to about 70 weight percent, based on the total weight of the block copolymer. In other embodiments, one or more second blocks are present in an amount of about 10 weight percent to about 50 weight percent or about 10 weight percent to about 30 weight percent.

Further, in some embodiments, the total amount of one or more second blocks in a block copolymer described herein is greater than the total amount of one or more first blocks. For example, in some cases, the weight ratio of second blocks to first blocks is at least about 1.5:1, 2:1, 3:1, 4:1, 5:1, 10:1, 15:1, or 20:1. In some embodiments, the weight ratio of second blocks to first blocks is up to about 1000:1, up to about 100:1, or up to about 50:1. Such a ratio of first and second blocks, in some instances, can provide a block copolymer primarily exhibiting the properties of the polymer or oligomer of the second block while also exhibiting fluorescence or luminescence due to the presence of the first block. Alternatively, in other instances, the total amount of one or more second blocks in a block copolymer described herein is less than or substantially equal to the total amount of one or more first blocks. In some embodiments, the weight ratio of second blocks to first blocks is between about 20:1 and about 1:20, between about 10:1 and about 1:10, between about 5:1 and about 1:5, between about 4:1 and about 1:4, between about 3:1 and about 1:3, between about 2:1 and about 1:2, or between about 1.5:1 and about 1:1.5.

Additionally, as described above, the identities and/or relative amounts of first and second blocks of a block copolymer described herein can be selected to provide a block copolymer having one or more desired properties. For example, in some cases, the biodegradability, photoluminescence, mechanical properties, and/or thermal properties of a block copolymer described herein can be selected based on the chemical identities and relative amounts of monomers and/or polymer blocks used to form the block copolymer. Similarly, in some instances, the first and second blocks are selected to provide an amphiphilic block copolymer. In some such embodiments, the second block comprises or is formed from a hydrophilic polymer or oligomer described herein, and the first block comprises or is formed from a hydrophobic polymer or oligomer formed from the reaction product of (i) a polycarboxylic acid or a polycarboxylic acid equivalent, (ii) a hydrophobic diol, and (iii) an amino acid. In addition, as an alternative to the embodiments described above, it is also possible to form a block copolymer using at least one hydrophobic block comprising a hydrophobic polymer or oligomer and at least one hydrophilic block comprising a hydrophilic polymer or oligomer, wherein the hydrophilic polymer or oligomer (instead of or in addition to the hydrophobic polymer or oligomer) is formed from the reaction product of (i) a polycarboxylic acid or a polycarboxylic acid equivalent, (ii) a diol, and (iii) an amino acid. In such cases, the polycarboxylic acid, polycarboxylic acid equivalent, and amino acid can comprise a polycarboxylic acid, polycarboxylic acid equivalent, and amino acid described hereinabove. However, the diol, in some implementations, comprises a hydrophilic diol rather than a hydrophobic diol. In some cases, for instance, the diol comprises a poly(ethylene glycol) rather than a poly(propylene glycol). Other hydrophilic macrodiols or small molecule diols can also be used. Further, the hydrophobic polymer or oligomer of such an alternative block copolymer described herein can comprise any hydrophobic polymer or oligomer not inconsistent with the objectives of the present disclosure. In some cases, for instance, the hydrophobic polymer or oligomer comprises a polyester or a polyolefin. In addition, in some embodiments, the hydrophobic polymer or oligomer can itself comprise a block copolymer described herein, such as a block copolymer comprising a polylactone block.

In some embodiments, a block copolymer described herein has the structure of Formula (VI):

A-B-A  (VI), wherein

B is a first block comprising a polymer or oligomer formed from the reaction product of (i) a polycarboxylic acid or a polycarboxylic acid equivalent, (ii) a polyol, and (iii) an amino acid; and each A is independently a second block comprising a polylactone. In some cases, each A independently comprises or is formed from a polymer or oligomer having the structure of Formula (III), Formula (IV), or Formula (V) above. Each A block may comprise or be formed from other monomer units as well, including any lactone species described hereinabove. Additionally, in some embodiments, each A block may be formed from the same monomer units. For example, each A may be a poly-D,L-lactide block, a poly-D-lactide block, a poly-L-lactide block, a polyglycolide block, a polycaprolactone block such as a poly-ε-caprolactone block, or a block formed from a mixture of monomers, such as a PLGA block. In other instances, each A block may be different. As one example, a first A block may be a poly-D,L-lactide block, and a second A block may be a poly-ε-caprolactone block. In addition, each A block may comprise or be formed from random copolymers of two or more different lactone monomers described herein.

Block copolymers described herein may be prepared in any manner not inconsistent with the objectives of the present disclosure. For example, in some cases, a first block of a block copolymer described herein may be prepared by providing a mixture of a polycarboxylic acid or polycarboxylic acid equivalent, a polyol, and an amino acid; increasing the temperature of the mixture to melt the mixture; and lowering the temperature of the mixture with stirring to form a polymer or oligomer. Additionally, in some cases, the resulting polymer or oligomer can be further purified by precipitating the polymer or oligomer and/or by dialysis.

Further, in some embodiments, a block copolymer described herein can be prepared by first providing a polymer or oligomer of a first block and a polymer or oligomer of a second block, and then coupling the two polymers or oligomers to form the block copolymer. As described further herein, such a method, in some cases, can provide a statistical or random block copolymer, or an alternating block copolymer such as an A-B-A block copolymer. In some embodiments, for instance, a method of making a block copolymer described herein comprises (a) providing a hydrophilic (or hydrophobic) polymer or oligomer described herein; (b) combining (i) a polycarboxylic acid or a polycarboxylic acid equivalent described herein, (ii) a polyol described herein, and (iii) an amino acid described herein to form a hydrophobic (or hydrophilic) polymer or oligomer described herein; and (c) coupling the hydrophilic polymer or oligomer to the hydrophobic polymer or oligomer. In addition, in some embodiments, providing a hydrophilic or hydrophobic polymer or oligomer comprises functionalizing the hydrophilic or hydrophobic polymer or oligomer with a carboxylic acid moiety, including in a manner described hereinabove. For example, in some embodiments, providing a hydrophilic polymer or oligomer comprises reacting a hydrophilic polymer or oligomer comprising a hydroxyl group with an acid anhydride such as succinic anhydride to provide a corresponding carboxylic acid of the hydrophilic polymer or oligomer. Such a carboxylic acid terminated hydrophilic polymer or oligomer, in some cases, can form an ester linkage with a hydrophobic polymer or oligomer described herein. More generally, coupling of two polymers or oligomers described herein to provide a block copolymer can be carried out in any manner not inconsistent with the objectives of the present disclosure. In some embodiments, for instance, coupling comprises forming an ester bond or linkage between the polymers or oligomers. Moreover, in some cases, coupling is carried out using a coupling agent and/or a coupling catalyst. For example, in some instances, coupling is carried out using a carbodiimide coupling scheme, such as a N,N'-dicyclohexylcarbodiimide (DCC) and 4-dimethylaminopyridine (DMAP) coupling scheme. However, as understood by one of ordinary skill in the art, coupling can be carried out in other ways as well.

It is also possible, in other cases, to prepare a block copolymer described herein by forming a polymer or oligomer of one block of the block copolymer in the presence of a previously prepared polymer or oligomer of another block of the block copolymer. For example, in some cases, a method of making a block copolymer comprises providing a mixture of a polycarboxylic acid or polycarboxylic acid equivalent, a polyol, and an amino acid; increasing the temperature of the mixture to melt the mixture; lowering the temperature of the mixture with stirring to form a first polymer or oligomer; mixing the first polymer with lactone monomers and a catalyst to form a second mixture; and heating the second mixture to form the block copolymer. In some embodiments, a block copolymer is prepared by first preparing a first block described herein, followed by ring-opening polymerization of one or more lactones or cyclic esters to form one or more second blocks comprising a polylactone. The ring-opening polymerization may be initiated by two terminal hydroxyl groups on the polymer or oligomer of the first block. Such a polymerization may be catalyzed by any suitable catalyst not inconsistent with the objectives of the present disclosure, including but not limited to one or more metal-containing compounds, such as metal alkoxides or metal carboxylates. Non-limiting examples of catalysts suitable for use in some embodiments described herein include tin or aluminum complexes, such as tin or aluminum alkoxides such as tin (II) 2-ethylhexanoate or tin (II) octoate. Other catalysts can include nucleophilic catalysts such as 1,8-diazabicyclo[5.4.0]undec-7-ene (DBU). A ring-opening polymerization may also be catalyzed by an enzyme such as a lipase (e.g., porcine pancreas lipase).

Further, it is to be understood that block copolymers and/or other polymers or oligomers described herein may include a variety of terminal or end groups. For example, a block copolymer may have end groups selected from hydroxy, alkoxy, aryloxy and ester groups. Moreover, the end groups of a block copolymer, in some embodiments, may not be further modified after preparation of the block copolymer. Alternatively, in other cases, the end groups of a block copolymer may be modified, including by adding a capping group or protecting group. For example, in some embodiments, a hydroxy end group of a block copolymer described herein can be alkylated or arylated to form an alkoxy- or aryloxy-capped block copolymer.

In addition, one or more pendant functional groups or moieties of a block copolymer described herein, such as one or more carboxyl or hydroxyl moieties, can further be used for surface modification of a block copolymer described herein, including with collagen, laminin, an RGD (Arg-Gly-Asp) peptide, a folate, and/or an aptamer. Such surface modification of a block copolymer, in some embodiments, can provide a desired cell adhesion, biodistribution, proliferation, and/or targeting profile to the block copolymer or secondary structure of the block copolymer.

II. Secondary Structures of Block Copolymers

In another aspect, secondary structures of block copolymers are described herein. In some cases, a secondary structure comprises a micelle or nanoparticle. In other instances, a secondary structure comprises a film. In still other embodiments, a secondary structure comprises a graft or scaffold. As described further herein, such secondary structures can be formed from any block copolymer not inconsistent with the objectives of the present disclosure. In some cases, a secondary structure described herein is formed from a block copolymer described hereinabove in Section I. Further, in some embodiments, a block copolymer used to form a secondary structure is an amphiphilic block copolymer. In other cases, a secondary structure is formed from a hydrophilic or hydrophobic block copolymer.

For example, in some embodiments, a micelle is formed from an amphiphilic block copolymer described hereinabove in Section I. Any amphiphilic block copolymer not inconsistent with the objectives of the present disclosure may be used. In some cases, a micelle is formed from an amphiphilic polymer, the amphiphilic polymer comprising (a) at least one hydrophilic block comprising a hydrophilic polymer or oligomer and (b) at least one hydrophobic block comprising a hydrophobic polymer or oligomer. The hydrophilic polymer or oligomer and/or the hydrophobic polymer or oligomer is formed from the reaction product of (i) a polycarboxylic acid or a polycarboxylic acid equivalent, (ii) a polyol, and (iii) an amino acid. In addition, in some embodiments, the hydrophilic block and the hydrophobic block are bonded together through an ester linkage.

A micelle formed from a block copolymer described herein can exhibit one or more properties of the block copolymer. For example, in some cases, a micelle described herein is a fluorescent or luminescent micelle. Not intending to be bound by theory, it is believed that the fluorescence or luminescence of a micelle described herein can emanate from one or more 6-membered rings of one or more block copolymers described herein that are used to form the micelle. Therefore, in some embodiments, a micelle described herein can be fluorescent without the addition of a separate fluorophore to the micelle, such as a quantum dot or a small molecule organic fluorophore such as a rhodamine or cyanine. In addition, the fluorescence wavelength of a micelle described herein can, in some cases, be selected based on the amino acid used to form a hydrophilic and/or hydrophobic block of a block copolymer used to form the micelle, as described further hereinbelow. Moreover, in some embodiments, a micelle described herein exhibits excitation-dependent emission.

A fluorescent micelle described herein, in some cases, can have a quantum yield of up to about 50 percent or up to about 30 percent. In some embodiments, a fluorescent micelle has a quantum yield between about 3 percent and about 50 percent, between about 4 percent and about 40 percent, or between about 5 percent and about 30 percent.

In addition, a fluorescent micelle described herein, in some instances, can have a high molar absorption coefficient, including a molar absorption coefficient that is higher than the molar absorption coefficient of the micelle building blocks. The micelle "building blocks," for reference purposes herein, comprise the one or more block copolymers used to form the micelle as well as subcomponents of the block copolymers, such as a hydrophobic block of a block copolymer. In some cases, for instance, a micelle has a molar absorption coefficient that is at least about 5 times or at least about 10 times the molar absorption coefficient of the block copolymer used to form the micelle. In some embodiments, a micelle described herein has a molar absorption coefficient between about $1000 \text{ L mol}^{-1} \text{ cm}^{-1}$ and about $10,000 \text{ L mol}^{-1} \text{ cm}^{-1}$ or between about $1500 \text{ L mol}^{-1} \text{ cm}^{-1}$ and about $6000 \text{ L mol}^{-1} \text{ cm}^{-1}$. Therefore, in some embodiments, a fluorescent micelle described herein can have a brightness that is comparable to or greater than the brightness of a fluorophore having the same or a higher quantum yield than the fluorescent micelle. "Brightness," for reference purposes herein, refers to the product of the quantum yield and the molar absorption coefficient of a fluorophore, such as a fluorescent micelle described herein. Fluorescent micelles described herein can also exhibit a high photostability.

Moreover, micelles described herein can have any size not inconsistent with the objectives of the present disclosure. In some instances, a micelle has a diameter of less than about 500 nm, less than about 250 nm, less than about 200 nm, less than about 100 nm, or less than about 50 nm when measured by transmission electron microscopy (TEM) or dynamic light scattering (DLS). In some cases, a micelle has a diameter between about 30 nm and about 500 nm, between about 30 nm and about 250 nm, or between about 50 nm and about 200 nm. Further, the size of a micelle described herein can be selected, in some embodiments, by varying the molecular weight of one or more of the hydrophilic polymers or oligomers of the hydrophilic block and the hydrophobic polymers or oligomers of the hydrophobic block. Further, the molecular weight of a hydrophilic or hydrophobic polymer or oligomer, in some cases, can be selected based on the molecular weight of the polyol used to form the hydrophilic or hydrophobic polymer or oligomer.

In addition, the size distribution of a population of micelles described herein, in some embodiments, can be monodisperse or substantially monodisperse. In some cases, a population of micelles can have a polydispersity measured as described herein of about 0.1 to about 0.3 or about 0.15 to about 0.22.

Micelles described herein can also have a negative zeta potential in aqueous solution. For example, in some embodiments, a micelle has a zeta potential between about −20 mV and about −30 mV.

Moreover, micelles described herein can also be thermodynamically stable compared to other micelles. For example, in some embodiments, a micelle described herein has a critical micelle concentration (CMC) of less than about 1 mg/mL, less than about 0.1 mg/mL, or less than about 0.01 mg/mL, based on the weight of the block copolymer used to form the micelle and the volume of a solvent in which the block copolymer is dispersed. In some instances, a micelle has a CMC between about 0.002 mg/mL and about 0.1 mg/mL, between about 0.002 mg/mL and about 0.05 mg/mL, or between about 0.004 mg/mL and about 0.02 mg/mL. The "CMC" of a micelle, for reference purposes herein, refers to the concentration of a block copolymer micelle building block above which micelles form and all additional block copolymer added to the system becomes part of micelles. In other words, at a block copolymer concentration above the CMC, micelles will form and all additional block copolymers added to the system will become part of micelles. The CMC can be determined in any manner not inconsistent with the objectives of the present disclosure. Further, the CMC of a micelle described herein can be selected, in some embodiments, by varying the zeta potential of the micelle and/or the molecular weight of one or more of the hydrophilic polymers or oligomers of the hydrophilic block and one or more hydrophobic polymers or oligomers of the hydrophobic block used to form the micelle.

Additionally, in some cases, a micelle described herein is a water-soluble or water-dispersable micelle having a hydrophobic core and a hydrophilic corona. Moreover, in some embodiments, such a micelle can further comprise a drug disposed in the hydrophobic core of the micelle. Any drug not inconsistent with the objectives of the present disclosure may be used. In some embodiments, for example, a drug comprises an anti-cancer drug such as Paclitaxel (PTX). Further, a drug described herein, in some cases, is lyophilic or water-insoluble.

Moreover, in some cases, a micelle comprising a drug as described herein can also be a fluorescent micelle. Therefore, as described further hereinbelow, such a micelle can be used for imaging, therapeutic, and/or theranostic applications.

Micelles described herein can be made in any manner not inconsistent with the objectives of the present disclosure. In some cases, a method of making a micelle comprises providing a block copolymer described hereinabove, adding the block copolymer to an aqueous solution, and forming the micelle by self-assembly of the block copolymer. Any block copolymer described hereinabove not inconsistent with the objectives of the present disclosure may be used. For example, in some embodiments, the block copolymer comprises (a) at least one hydrophilic block comprising a hydrophilic polymer or oligomer and (b) at least one hydrophobic block comprising a hydrophobic polymer or oligomer, wherein the hydrophobic polymer or oligomer is formed from the reaction product of (i) a polycarboxylic acid or a polycarboxylic acid equivalent, (ii) a diol, and (iii)

an amino acid. In addition, in some embodiments, the hydrophilic block and the hydrophobic block are bonded together through an ester linkage. Further, in some cases, the aqueous solution comprises a drug and the method further comprises encapsulating the drug in the core of the micelle during self-assembly of the micelle.

Secondary structures of block copolymers described herein can also comprise nanoparticles. Nanoparticles of block copolymers described herein can have any size and shape not inconsistent with the objectives of the present disclosure. In some cases, nanoparticles of block copolymers are spherical or substantially spherical. In some instances, nanoparticles of block copolymers are oblate or anisotropic. Nanoparticles described herein, in some embodiments, have an aspect ratio between about 1 and about 2, between about 1 and about 1.5, between about 1 and about 1.3, between about 1 and about 1.2, or between about 1 and about 1.1. Further, in some cases, nanoparticles of block copolymers described herein have a size in two or three dimensions between about 10 nm and about 1000 nm, between about 50 nm and about 500 nm, or between about 100 nm and about 300 nm.

Secondary structures of block copolymers described herein can also comprise films or grafts or scaffolds. In some embodiments, a film and/or scaffold described herein comprises a dried and/or crosslinked block copolymer described hereinabove. A block copolymer described herein can be crosslinked in any manner not inconsistent with the objectives of the present disclosure. In some cases, for instance, a block copolymer is crosslinked through one or more side chains or pendant groups of the block copolymer, such as through one or more ethyleneically unsaturated moieties pendant to the block copolymer. A block copolymer may also be crosslinked through a pendant carboxyl, carboxylate, or hydroxyl moiety.

A film and/or scaffold of a block copolymer described herein can be prepared in any manner not inconsistent with the objectives of the present disclosure. For example, as described further hereinbelow, a scaffold can be formed by salt leaching, casting, and/or molding. Similarly, in some cases, nanoparticles of a block copolymer described herein can be formed by emulsification/evaporation.

Secondary structures such as micelles, nanoparticles, films, and scaffolds described herein, in some embodiments, can be used for a variety of biological and/or biomedical applications, including one or more tissue engineering applications. In some cases, for instance, a scaffold described herein can be used to non-invasively monitor the degradation of a biological implant or other material and/or to monitor a foreign body response in vivo. In addition, in some embodiments, a structure formed from one or more block copolymers described herein can be used for blood vessel, bone, skin, cardiac, and other tissue engineering applications. Such a structure can be used to provide mechanical support to tissue, to facilitate tissue growth, to image a biological compartment, and/or to deliver one or more drugs or other therapeutic compositions to a biological compartment, including in a targeted or site-selective manner. Further, a structure described herein can also provide a fluorescence signal in vivo or in vitro, including in response to a biological event or non-biological event, such as a physical or chemical degradation event.

In some embodiments, a secondary structure described herein forms an article such as a medical device. A medical device formed from one or more block copolymers described herein, in some cases, can be an orthopedic fixation device (including but not limited to an orthopedic screw), a tissue graft, a fiber, or a suture. Other articles and/or medical devices may also be formed from one or more block copolymers described herein.

III. Methods of Imaging a Biological Compartment

In another aspect, methods of imaging a biological compartment are described herein. In some embodiments, a method of imaging comprises disposing a structure described hereinabove in Section II in a biological compartment and using the structure to image the compartment. Any structure described hereinabove in Section II may be used. For example, in some cases, a method of imaging comprises disposing a micelle formed from an amphiphilic polymer in a biological compartment; irradiating the micelle with electromagnetic radiation at least partially overlapping the absorption profile of the amphiphilic polymer to induce fluorescence or luminescence from the amphiphilic polymer; and detecting the fluorescence or luminescence with a detector, wherein the amphiphilic polymer comprises a block copolymer described herein. Any amphiphilic block copolymer described hereinabove in Section I may be used. In some embodiments, for instance, the amphiphilic polymer comprises (a) at least one hydrophilic block comprising a hydrophilic polymer or oligomer and (b) at least one hydrophobic block comprising a hydrophobic polymer or oligomer, wherein the hydrophobic polymer or oligomer is formed from the reaction product of (i) a polycarboxylic acid or a polycarboxylic acid equivalent, (ii) a diol, and (iii) an amino acid. In addition, in some embodiments, the hydrophilic block and the hydrophobic block are bonded together through an ester linkage. In addition, the micelle formed from the amphiphilic polymer can have any structure and/or properties of a micelle described hereinabove in Section II. For example, in some cases, the micelle is a nanoparticulate micelle.

Turning now to steps of methods, methods of imaging a biological compartment described herein comprise disposing a micelle, or other structure comprising a block copolymer, in a biological compartment. The micelle or other structure can be disposed in the biological compartment in any manner not inconsistent with the objectives of the present disclosure. For example, in some cases, the micelle or other structure is disposed in the biological compartment intravenously, subcutaneously, or in an intraperitoneal manner. In some instances, a micelle or other structure is injected into the biological compartment as an aqueous solution. In addition, a micelle or other structure can be disposed in any biological compartment not inconsistent with the objectives of the present disclosure. In some cases, the biological compartment is a blood vessel. In other instances, the biological compartment is diseased tissue. In some embodiments, the biological compartment is healthy tissue.

Methods of imaging a biological compartment described herein also comprise irradiating the micelle or other structure with electromagnetic radiation at least partially overlapping the absorption profile of the amphiphilic polymer of the micelle or other structure to induce fluorescence or luminescence from the amphiphilic polymer. Irradiation can be carried out in any manner not inconsistent with the objectives of the present disclosure. In some embodiments, for instance, the micelle or other structure is irradiated with electromagnetic radiation having a wavelength in the visible portion of the electromagnetic spectrum. In other instances, the micelle is irradiated with ultraviolet (UV), near infrared (NIR), or infrared (IR) radiation. In some embodiments, the irradiation wavelength is chosen based on the absorption profile of the biological compartment in addition to the absorption profile of the block copolymer or other structure.

Methods of imaging tissue described herein also comprise detecting fluorescence or luminescence with a detector. Any detector not inconsistent with the objectives of the present invention may be used. In some embodiments, for example, the detector comprises a charge-coupled device (CCD) image sensor or camera.

IV. Methods of Treating Diseased Tissue

In another aspect, methods of treating diseased tissue are described herein. In some embodiments, a method of treating diseased tissue comprises disposing a structure described hereinabove in Section II in a biological compartment. In some cases, the structure comprises a drug or other therapeutic composition. For example, in some embodiments, a method of treating diseased tissue comprises (a) disposing a micelle in a biological compartment, the micelle comprising a hydrophobic core, a hydrophilic corona, and a drug disposed in the hydrophobic core; and (b) releasing the drug into the biological compartment. The micelle can have the structure and/or properties of any micelle described hereinabove in Section II. For example, in some instances, the micelle is formed from an amphiphilic polymer comprising (a) at least one hydrophilic block comprising a hydrophilic polymer or oligomer and (b) at least one hydrophobic block comprising a hydrophobic polymer or oligomer, wherein the hydrophobic polymer or oligomer is formed from the reaction product of (i) a polycarboxylic acid or a polycarboxylic acid equivalent, (ii) a diol, and (iii) an amino acid. Other micelles may also be used.

Further, the drug disposed in the hydrophobic core of the micelle can also comprise any drug not inconsistent with the objectives of the present disclosure. In some embodiments, for instance, a drug comprises an anti-cancer drug such as Paclitaxel. Further, a drug described herein, in some cases, is lyophilic or water-insoluble. Moreover, the biological compartment in which the micelle is disposed and into which the drug is released can comprise any biological compartment not inconsistent with the objectives of the present disclosure, including a biological compartment described hereinabove in Section III. In some cases, the biological compartment itself comprises the diseased tissue to be treated. In other cases, the biological compartment may facilitate transport or uptake of a released drug into diseased tissue located elsewhere.

Additionally, in some embodiments, a method of treating diseased tissue described herein can further comprise imaging the diseased tissue. For example, in some embodiments, a method described herein further comprises irradiating the micelle with electromagnetic radiation at least partially overlapping the absorption profile of the amphiphilic polymer of the micelle to induce fluorescence from the amphiphilic polymer; and detecting the fluorescence with a detector. As understood by one of ordinary skill in the art, such imaging can be carried out in any manner described hereinabove in Section III. Therefore, in some embodiments, a micelle described herein can be used for theranostic applications as well as imaging and/or therapeutic applications.

Some embodiments described herein are further illustrated in the following non-limiting examples.

EXAMPLE 1

Block Copolymers

A series of photostable fluorescent amphiphilic block copolymers according to some embodiments described herein were prepared as follows. For reference purposes, the block copolymers of the present Example are referred to as amphiphilic biodegradable photoluminescent polymers (ABPLPs), and the first blocks of the block copolymers are sometimes referred to as simply biodegradable photoluminescent polymers (BPLPs). Further, some BPLPs are denoted by the names of the species used to form the BPLPs. For example, a BPLP formed from L-cysteine can be referred to as BPLP-Cys. Similarly, a BPLP formed from citric acid (CA), poly(propylene glycol) (PPG), and L-cysteine can be referred to as PPGCA-Cys.

As illustrated in FIG. 1, methoxy poly(ethylene glycol) (MPEG) having a weight average molecular weight of 750, 2000, or 5000 was used to form the hydrophilic block (1) in the specific embodiments of FIG. 1. In step 1, MPEG was first converted to MPEG-COOH by reaction with succinic anhydride. Specifically, MPEG (20 mmol) was dissolved in anhydrous toluene (200 mL) in a 500 mL round bottom flask. Succinic anhydride (40 mmol) was added, and the reaction mixture was refluxed at 150° C. for 10 h. After the solution cooled, the residue was filtered out, and the remaining toluene was distilled under reduced pressure. Next, the polymer was dissolved in 20 mL hot water (70° C.). The collected organic phase was then dried with anhydrous $Na_2SO_4$, stirred overnight, filtered, and distilled under vacuum. 20 mL dry ethyl ether was then added drop wise into the 3 mL $CHCl_3$ polymer solution, and the top layer of ethyl ether was discarded. This extraction process was repeated three times, and the collected organic phase was finally dried under vacuum.

In step 2, the hydrophobic blocks (2) were synthesized from a polycarboxylic acid (citric acid), diol (PPG), and amino acid (L-cysteine). Briefly, PPG, citric acid, and L-cysteine with molar ratios of 1.1:1.0:0.2, respectively, were added to a 100 mL round bottom flask, and melted by continuous stirring at 160° C. The foregoing monomer ratios were chosen to provide hydrophobic blocks having terminal hydroxyl groups on both ends of the block. After melting the monomer mixture, the temperature of the system was lowered to 140° C., and the monomers were allowed to condense for 4 hours. Next, the polymer was dissolved in 1,4-dioxane and precipitated by drop-wise addition into deionized water under constant stirring. Finally, the purified BPLP was collected and dried using lyophilization.

In this process, the citric acid was reacted with PPG to form a polyester backbone and further condensed with L-cysteine via the pendent carboxyl group and geminal hydroxyl group of the citrate units to create a 6-membered ring. The 6-membered planar rings pendant on the BPLP polymer backbones were composed of amide and ester bonds with different R groups from the various amino acids. Not intending to be bound by theory, it is believed that the planar rings cause the polymer fluorescence through hyperconjugation. It is further believed that the R groups pendant to the α-C in the amino acids likely influence the degree of hyperconjugation and propensity for cyclization, and thus provide slight perturbations in the associated energy levels, resulting in the different emission maxima and quantum yields observed for the different BPLP-amino acids.

In step 3, the —COOH terminated hydrophilic MPEG chains were conjugated with the —OH terminated hydrophobic BPLP chains through DCC/DMAP chemistry to form ABPLPs (3). Briefly, 2.5 mmol of BPLP, 2.5 mmol MPEG-COOH, 0.5 mmol of N-dimethyl aminopyridine (DMAP), and 10 mmol of dicyclohexylcarbodiimide (DCC) were added to a 100 mL round bottom flask containing 50 mL of 1,4-dioxane at room temperature while stirring and maintained for 24 h. After 24 h, the precipitated dicyclohexylurea (DCU) was filtered out and the filtrate was concentrated under reduced pressure and quickly poured into a large amount of cold diethyl ether with vigorous stirring. After filtering under reduced pressure, the product was further placed in a dialysis bag (molecular weight cut-off 2 kDa) to remove any unreacted segments. After 72 h of dialysis, the purified product was collected via lyophilization.

Figure 3A:
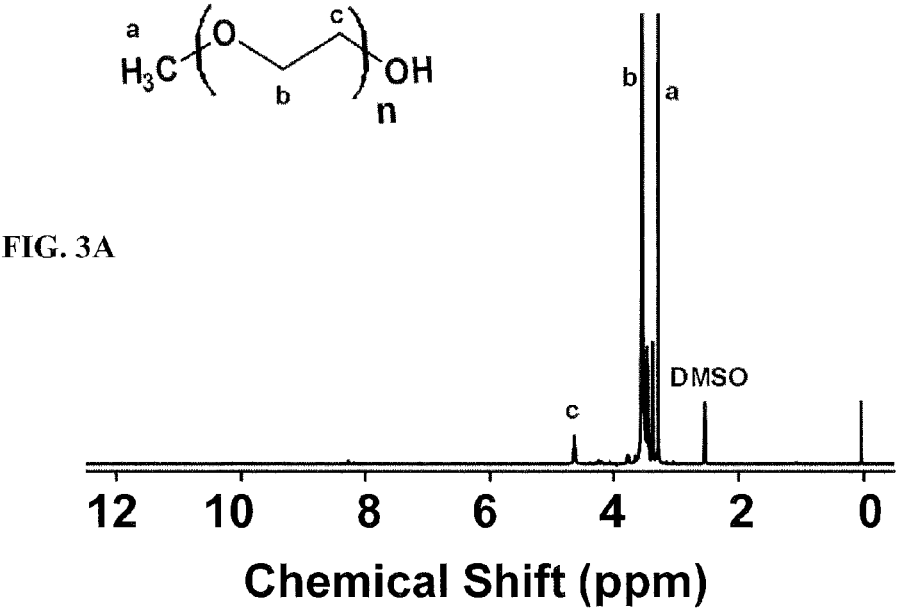
FIG. 3A and FIG. 3B each illustrates a proton nuclear magnetic resonance ($^1$H-NMR) spectrum of a component of a block copolymer according to one embodiment described herein.
Figure 3B:
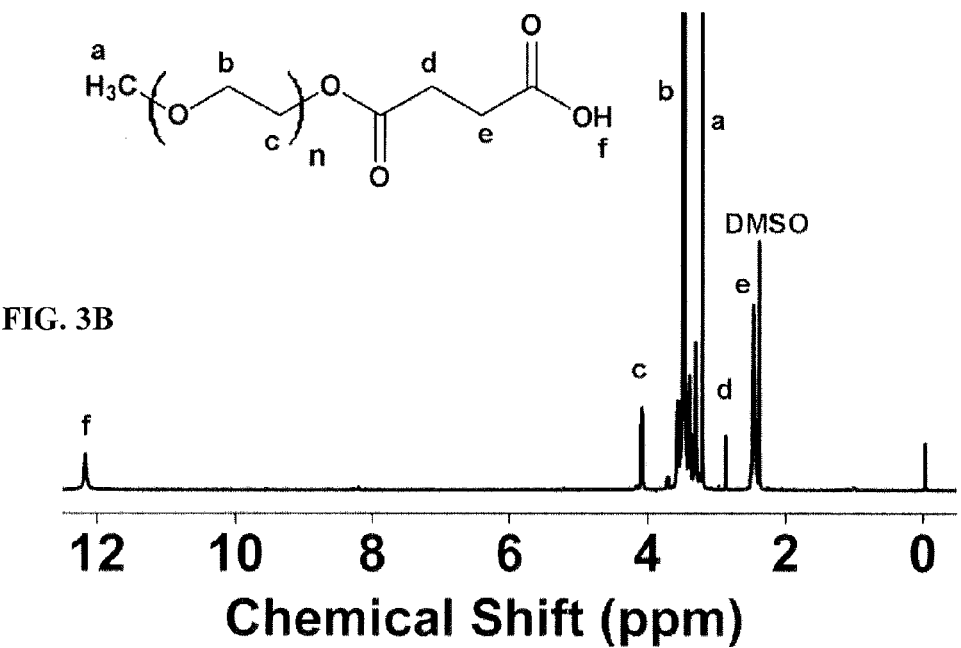
Figure 4A:
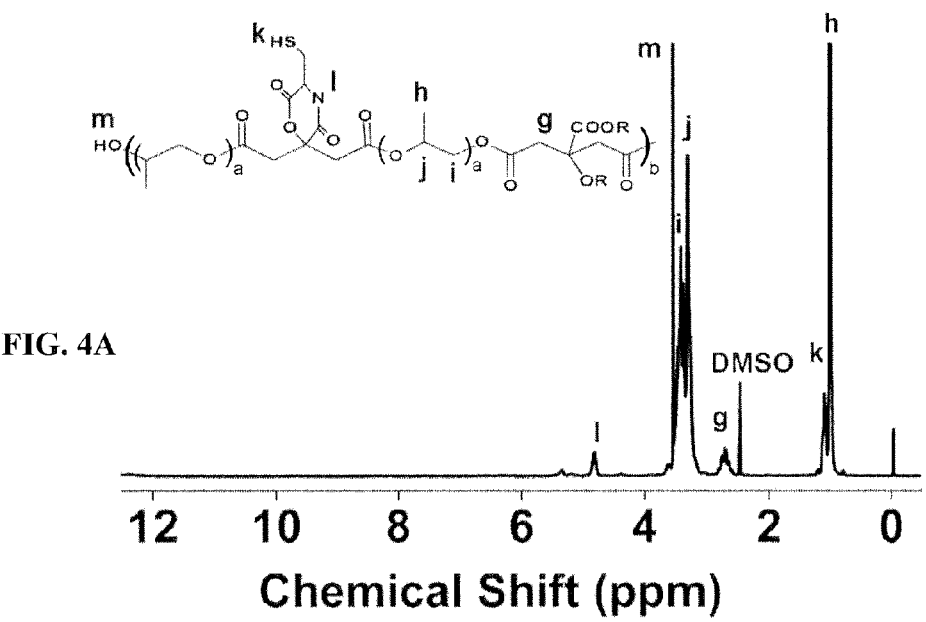
FIG. 4A and FIG. 4B each illustrates an $^1$H-NMR spectrum of a component of a block copolymer according to one embodiment described herein.
Figure 4B:
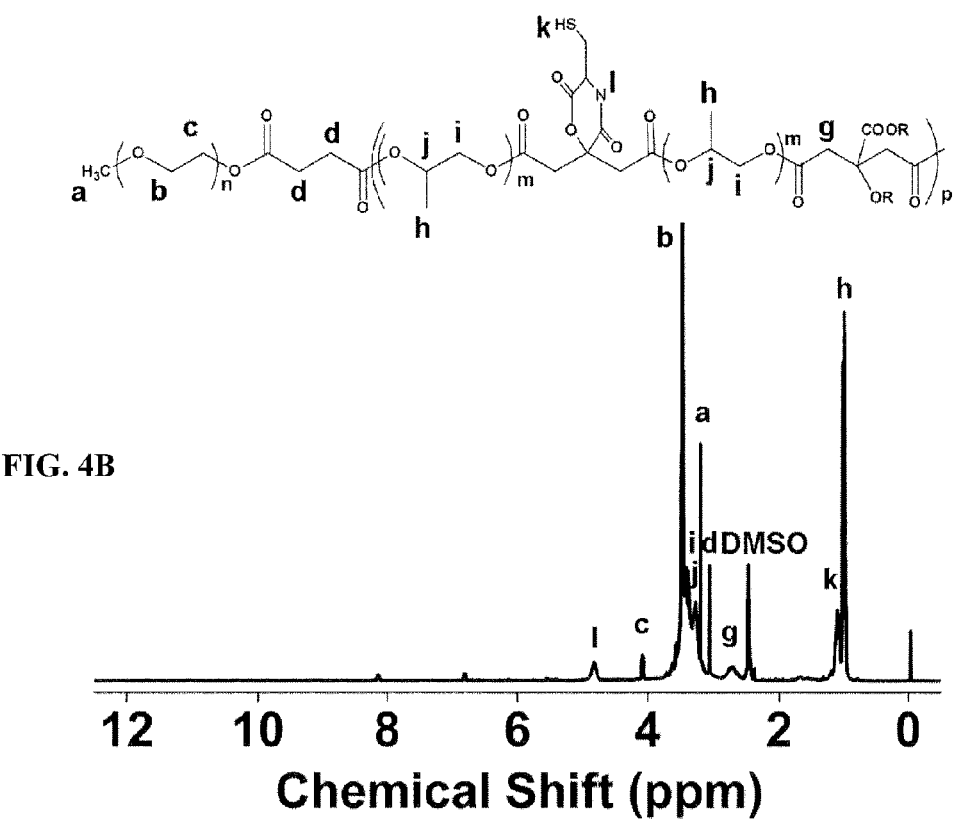

Characteristic bond vibrations were observed in Fourier Transform Infrared (FTIR) spectra (FIG. 2), and characteristic chemical shifts were observed in $^1$H-NMR spectra (FIG. 3 and FIG. 4) for the various chemical species described in the protocol above, confirming successful synthesis. For FTIR analysis, purified polymer was dissolved in acetone to make a 5.0 wt.-% solution. The polymer solution was then cast onto potassium bromide pellets, and the solvent was allowed to evaporate overnight prior to analysis with a Nicolet 6700 Fourier Transform Infrared (FTIR) spectrometer (Thermo Fisher Scientific). The FTIR spectra (FIG. 2) of the hydrophilic block (MPEG-COOH), the hydrophobic block (PPGCA-Cys), and the block copolymer (ABPLP-3) included a carbonyl peak at 1690-1750 cm$^{-1}$, a hydroxyl peak at 3400 cm$^1$ from succinic acid, a methylene peak at 2877 cm$^{-1}$, and an ether peak at 1112 cm$^{-1}$ from PEG. For $^1$H-NMR analysis, 5.0 mg of polymer was dissolved in 1.0 mL of deuterated dimethyl sulfoxide (DMSO-d$_6$). $^1$H-NMR spectra were collected at room temperature with tetramethylsilane used as an internal reference and using a 300 MHz JNMECS 300 (JEOL, Tokyo, Japan). FIG. 3 illustrates $^1$H-NMR spectra of (FIG. 3A) hydroxyl terminated MPEG and (FIG. 3B) carboxylic acid terminated MPEG (MPEG-COOH). The characteristic peaks (a and b) of MPEG located at 3.2 and 3.6 ppm assigned to —C$\underline{H}_3$ and —C$\underline{H}_2$, respectively, were shown at the same chemical shift for both MPEG and MPEG-COOH. However, the peak (c) at 4.6 ppm assigned to C$\underline{H}_2$—OH of MPEG shifted to 4.1 ppm due to the conversion of MPEG to MPEG-COOH. Protons (d and e) of methylene groups from succinic acid at 2.8 and 2.2 ppm and protons (f) of COOH groups at 12.1 ppm were observed only on MPEG-COOH, confirming the successful termination of MPEG with carboxylic acid. FIG. 4A illustrates an $^1$H-NMR spectrum of hydroxyl terminated BPLP. The chemical shifts included an additional peak of the methyl group from poly(propylene glycol) at 1.1 ppm. FIG. 4B illustrates an $^1$H-NMR spectrum of BPLP conjugated to MPEG-COOH. All characteristic peaks from both hydrophobic and hydrophilic blocks were present in the copolymers, absent a COO$\underline{H}$ peak located at 12.1 ppm. It should be noted that proton e located at 2.3 ppm in FIG. 3B shifted to 3.1 ppm (labeled d in FIG. 4B), confirming the successful modification of the neighboring carboxylic groups into ester groups. Furthermore, a significant reduction in the hydroxyl peak was also observed in the FTIR spectrum of amphiphilic block copolymers when compared to the hydrophobic block spectrum alone (FIG. 2).

Various molecular weights of PPG (425, 725, and 2000 Da) and MPEG (750, 2000, and 5000 Da) were used to provide a series of ABPLPs. The ABPLPs could be dissolved in a variety of solvents, including acetone, tetrahydrofuran (THF), dimethylformamide (DMF), methyl chloride, and dimethylsulfoxide (DMSO). The ABPLPs could also form micelles when dispersed in aqueous solution, as described in Example 2.

EXAMPLE 2

Micelles

As amphiphilic copolymers, the ABPLPs of Example 1 were able to self-assemble into nano-sized micelles in an aqueous medium. Specifically, to prepare ABPLP micelle solutions, 100 mg of ABPLP was dissolved in 5.0 mL of acetone to make a 2.0% w/v solution. Then, 500 μL of the 2.0% w/v polymeric solution was added drop wise into 20 mL deionized water under gentle stirring. The acetone was allowed to evaporate at room temperature for several hours to produce an aqueous solution of micelles.

Figure 5:
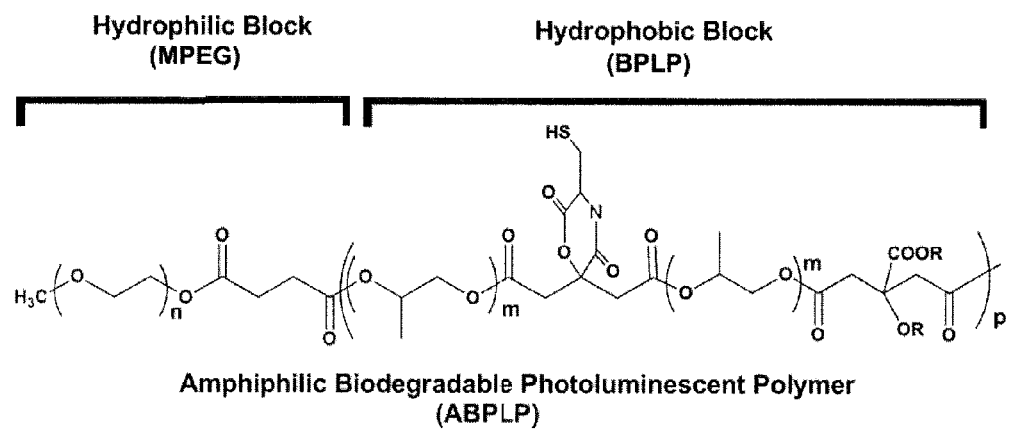
FIG. 5 illustrates the structure of a block copolymer according to one embodiment described herein.
Figure 6:
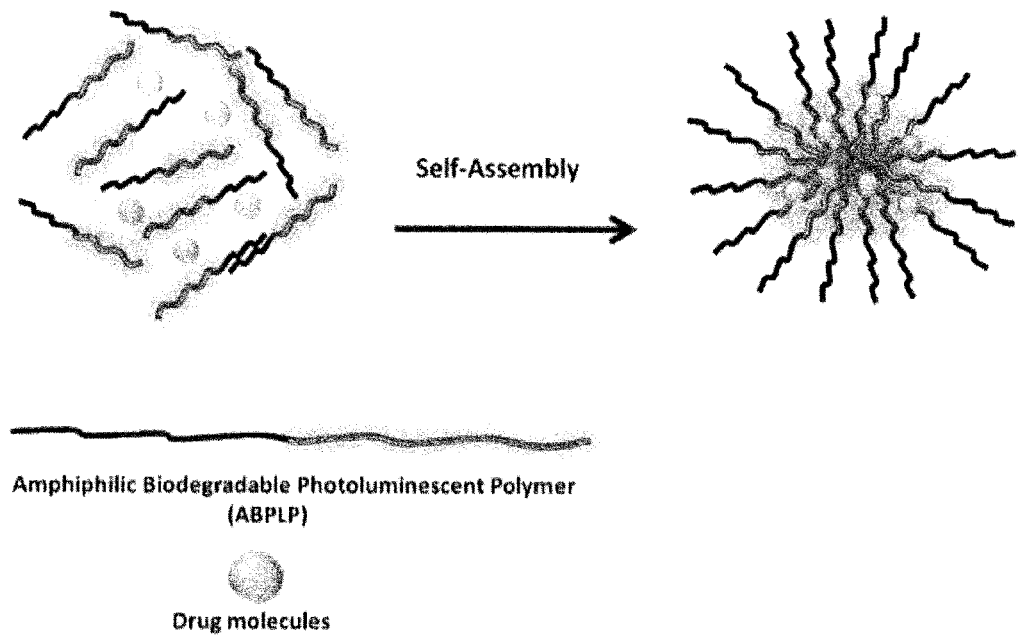
FIG. 6 illustrates a method of making a micelle according to one embodiment described herein.
Figure 7:
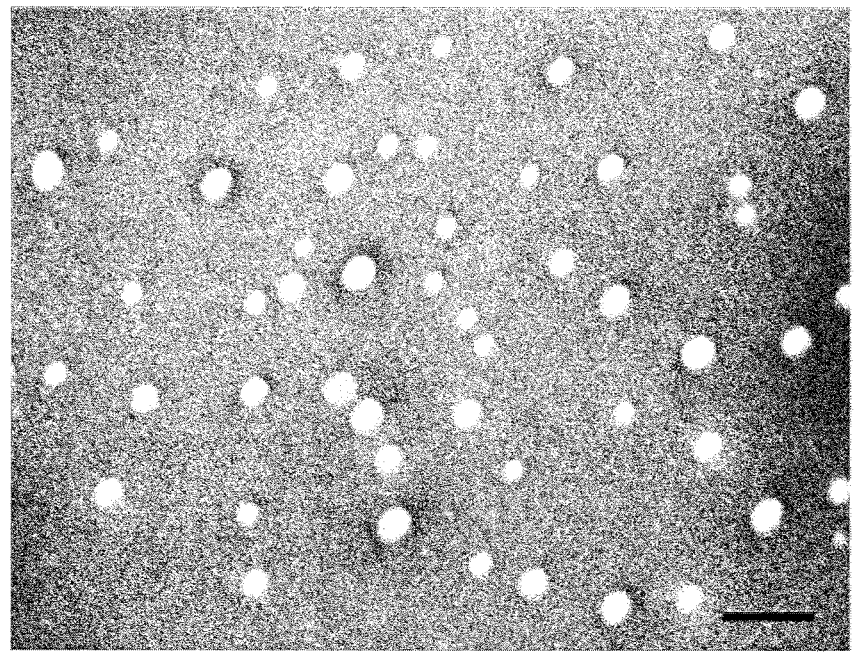
FIG. 7 illustrates a transmission electron microscopy (TEM) image of micelles according to one embodiment described herein.

FIG. 5 illustrates the structure of the ABPLPs, and FIG. 6 and FIG. 7 illustrate the formation of micelles from the ABPLPs. As illustrated in FIG. 6, ABPLP copolymers comprising fluorescent hydrophobic blocks can self-assemble into core-shell (micelle) structures encapsulating hydrophobic drugs within their core in an aqueous solution.

Figure 8:
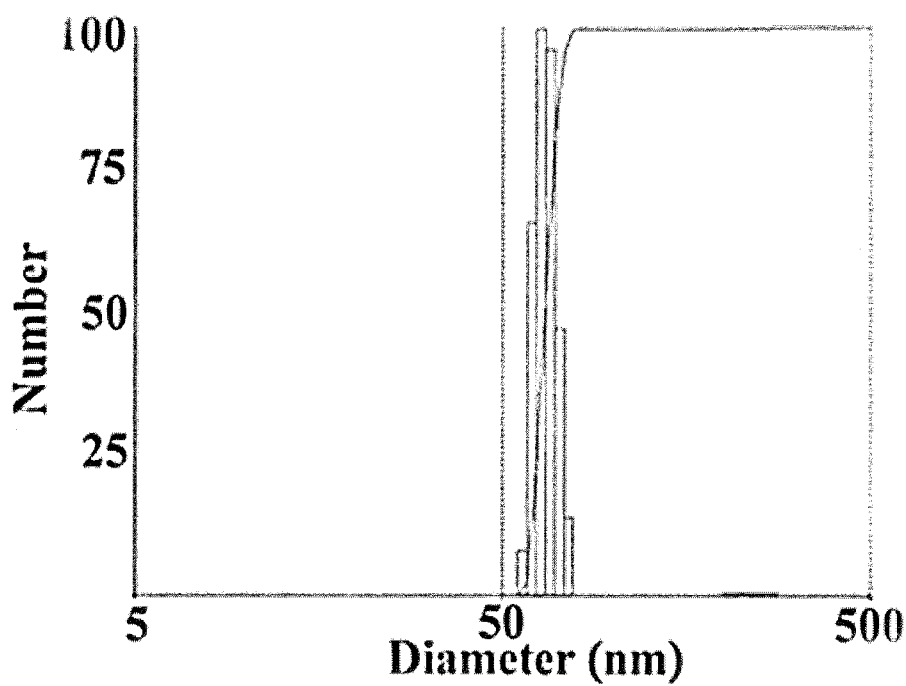
FIG. 8 illustrates the size distribution of a population of micelles according to one embodiment described herein.

Under transmission electron microscopy (TEM), ABPLP-3 micelles were spherical in shape and about 60 nm in diameter (FIG. 7), which was in agreement with the size measurements from dynamic light scattering (an average diameter of 68 nm and a polydispersity index of 0.17) (FIG. 8). No particle aggregation was observed, and ABPLPs synthesized using low molecular weight PPG, as in the case of ABPLP-1 and ABPLP-2, demonstrated higher particle sizes of 178 and 107 nm, respectively. However, ABPLPs synthesized with higher molecular weight PPG, as in the case of ABPLP-3, exhibited smaller particle sizes of 68 nm. In addition, particle size was further reduced with an increase in the hydrophilic block molecular weight, as in the case of ABPLP-4 (53 nm) and ABPLP-5 (48 nm).

The thermodynamic stability of micelles was determined by the critical micelle concentration (CMC). Specifically, the CMC of amphiphilic copolymer in aqueous solution was determined by a fluorescence probe technique, where pyrene was used as a hydrophobic flourecent probe. The fluorescence spectra of the samples were acquired using a Shimadzu RF-5301 PC fluorospectrophotometer at room temperature. The pyrene-loaded micelle solution was prepared as described in Licciardi et al., *Int. J. Pharm.* 2010, 396, 219. Briefly, a known amount of pyrene in acetone was added into 10 mL vials and the acetone was allowed to evaporate. Next, aqueous ABPLP solutions at various concentrations (1×10$^{-4}$ to 10 mg/mL) with the final concentration of pyrene as 6.0×10$^{-7}$ M were prepared for further analysis. Excitation and emission spectra of pyrene were recorded at room temperature and the ratios of the peak intensities at 338 and 333 nm ($I_{338}/I_{333}$) of the spectra were analyzed as a function of polymer concentration. The CMC value was taken from the intersection of the tangent to the curve at the inflection with the horizontal tangent through the point at the low concentrations.

Figure 9:
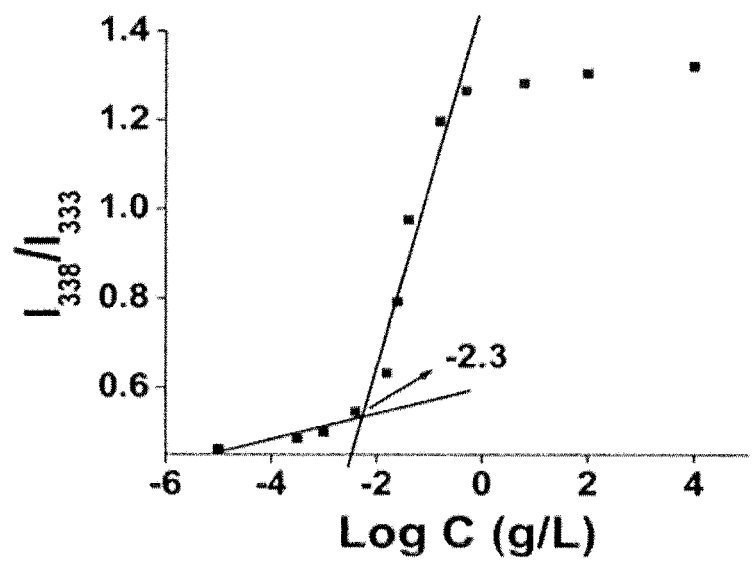
FIG. 9 illustrates a plot for determining the critical micelle concentration (CMC) of micelles according to some embodiments described herein.

FIG. 9 illustrates a plot of the intensity ratios $I_{338}/I_{333}$ pyrene versus the log of the concentration (C) of ABPLP-3 in aqueous medium. CMC values of 0.012, 0.006 and 0.004 mg/mL for ABPLP-1, ABLP-2 and ABPLP-3, respectively, in aqueous solution were seen to decrease as the fraction of the PPG hydrophobic block in the amphiphilic copolymers increased. On the other hand, the CMC values for ABPLP-3, ABPLP-4, and ABPLP-5 were calculated as 0.004, 0.005, and 0.010 mg/mL, respectively. These results are provided in Table I below. When the length of the hydrophobic block remained constant, the CMC values increased in relation to an increasing hydrophilic block (MPEG) length, possibly due to increased hydrophilicity. The lower CMC values for ABPLPs suggest that the ABPLP micelles are potentially more stable after intravenous administration. Based on the "salt out" effect, an even lower CMC value may be expected for micelles in ionic blood solution.

TABLE I

Some Properties of Block Copolymer Micelles.

| Polymer | PPG/MPEG | CMC (mg/mL) | Size (nm) | Polydispersity | Zeta Potential (mV) |
|---|---|---|---|---|---|
| ABPLP-1 | 425/750 | 0.012 | 178 ± 3.50 | 0.20 ± 0.05 | −23.57 ± 2.30 |
| ABPLP-2 | 725/750 | 0.006 | 107 ± 1.10 | 0.21 ± 0.06 | −21.81 ± 1.86 |
| ABPLP-3 | 2000/750 | 0.004 | 68 ± 0.80 | 0.18 ± 0.03 | −27.07 ± 3.00 |
| ABPLP-4 | 2000/2000 | 0.005 | 53 ± 0.70 | 0.17 ± 0.02 | −23.87 ± 2.22 |
| ABPLP-5 | 2000/5000 | 0.01 | 48 ± 0.60 | 0.16 ± 0.02 | −23.77 ± 1.28 |

Figure 10:
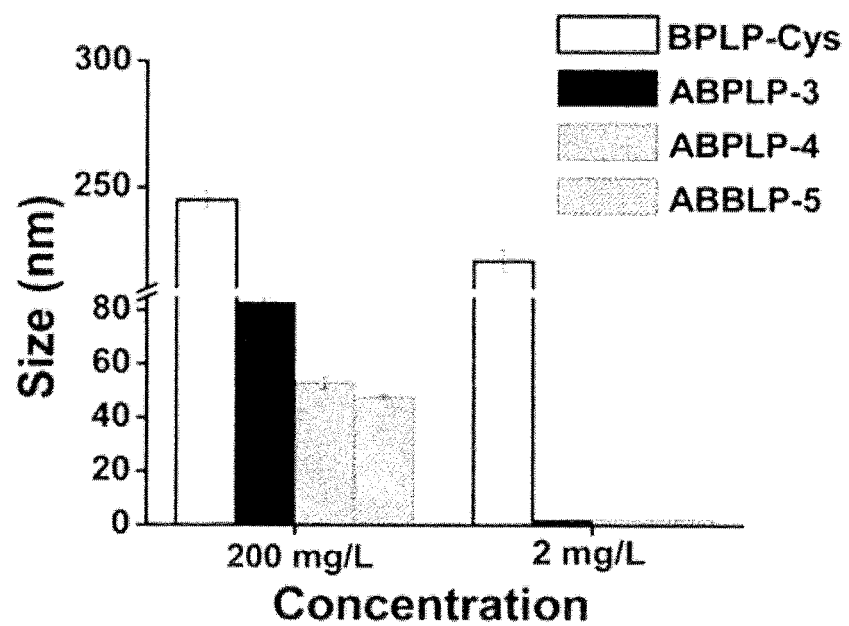
FIG. 10 illustrates the sizes of micelles according to some embodiments described herein.

To verify the micelle formation, the sizes of ABPLP micelles were measured by DLS at concentrations above and below the CMC for various ABPLP micelles and compared to the nanospheres of the corresponding BPLPs. Upon dilution below the CMC (0.002 mg/mL), all the ABPLP micelles completely disassembled and the sizes could not be detected by DLS, whereas BPLP nanospheres displayed stable solid colloidal solutions even at very low concentrations (FIG. 10). In addition, ABPLP micelles displayed a negative zeta potential in deionized water in the range of −20 to −27 mV (Table I), which may also contribute to the micelle stability, since the strong electrostatic repulsion may minimize micelle aggregation.

The hydrodynamic diameter, polydispersity, and surface charge of the ABPLP micelles and BPLP particles were measured at concentrations below and above CMC values using a zeta potential analyzer (ZetaPALS, Brookhaven Instruments, Holtsville, N.Y.) equipped with dynamic light scattering (DLS) detector. The morphology of the block copolymer micelles was characterized by transmission electron microscope (JEOL 1200 EX, Tokyo, Japan). The TEM was operated at an acceleration voltage of 80 kV. Samples for TEM observation were prepared by depositing a drop of polymeric micelles onto a mesh copper grid coated with carbon. After the deposition, the aqueous solution was blotted away with a strip of filter paper and allowed to dry.

The fluorescent properties of ABPLPs were also investigated, including in comparison to the corresponding BPLPs. Photoluminescent spectra of BPLP and ABPLP polymers and micelle solutions were acquired on a Shimadzu RF-5301 PC fluorospectrophotometer. The optimal excitation wavelength for each type of the micelle solution emission test was determined as the wavelength that generated the highest emission intensity. In this study, BPLPs and ABPLPs were excited at 360 nm, and the excitation and the emission slit widths were both set at 1.5 nm for all samples unless otherwise stated.

The fluorescence quantum yields of ABPLP in both solvent and in micelle form were measured using the method of Williams et al., *Analyst* 1983, 108, 1067. The solutions were scanned at optimal excitation wavelength. Then, the UV-vis absorbance spectrum was collected with the same solution and the absorbance at the optimal excitation wavelength was noted. Next, a series of solutions was prepared with gradient concentrations. The absorbance of each solution was controlled within the range of 0.01-0.1 Abs units. The fluorescence spectrum was also collected for the same solution in the 10 mm fluorescence cuvette. The fluorescence intensity, which is the area of the fluorescence spectrum, was calculated and noted. Polymer solutions with different concentrations were measured and the graphs of integrated fluorescence intensity vs. absorbance were plotted. The quantum yields of the ABPLPs were calculated according to equation (2):

$$\Phi_x = \Phi_{ST}\left(\frac{slope_x}{slope_{ST}}\right)\left(\frac{\eta_x}{\eta_{ST}}\right)^2, \quad (2)$$

wherein

Φ=quantum yield; slope=gradient of the curve obtained from the plot of intensity versus absorbance; η=refractive index of the solvent; x=subscript to denote the sample, and ST=subscript to denote the standard.

Figure 11:
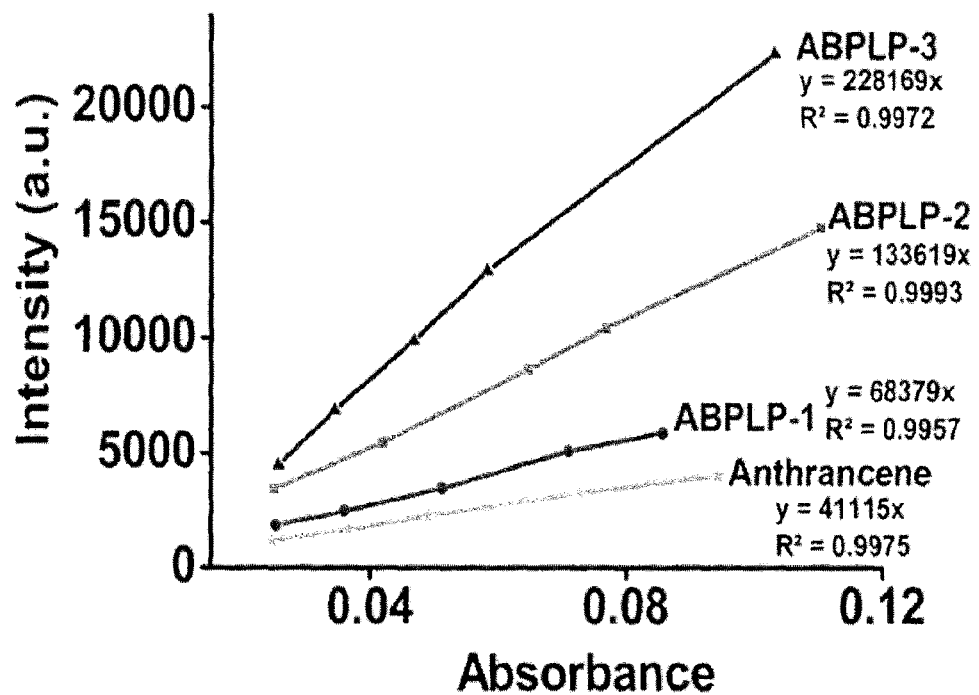
FIG. 11 and FIG. 12 each illustrates optical properties of micelles according to some embodiments described herein.

Anthracene (Φ=0.27 in ethanol) was used as a standard. The ABPLP polymers were dissolved in 1,4-dioxane and anthracene was dissolved in ethanol. The slit width was kept similar for both the standard and samples. Absorbance was measured using a Shimadzu UV-2450 spectrophotometer. The molar absorption coefficient (ε, L·mol$^{-1}$ cm$^{-1}$) of the BPLPs and ABPLPs was calculated according to the Beer-Lambert law, where A=εCL. All the experiments were carried out in triplicate. FIG. 11 illustrates intensity-absorbance curves of ABPLP-1, ABPLP-2, and ABPLP-3 for quantum yield measurements.

Figure 12:
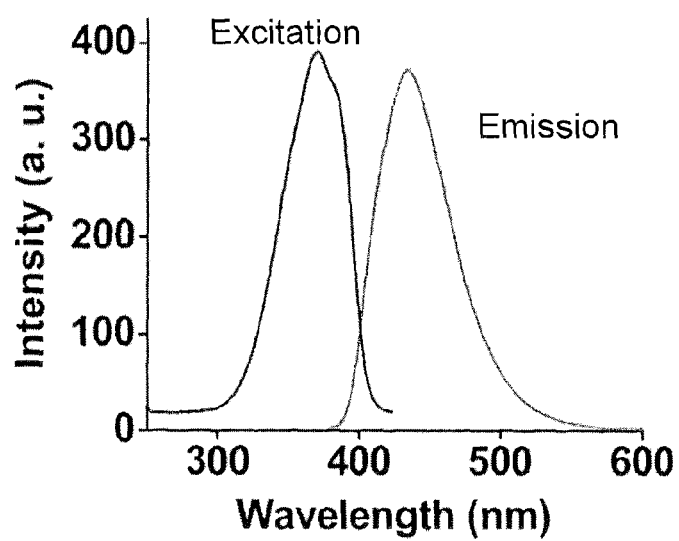
Figure 13:
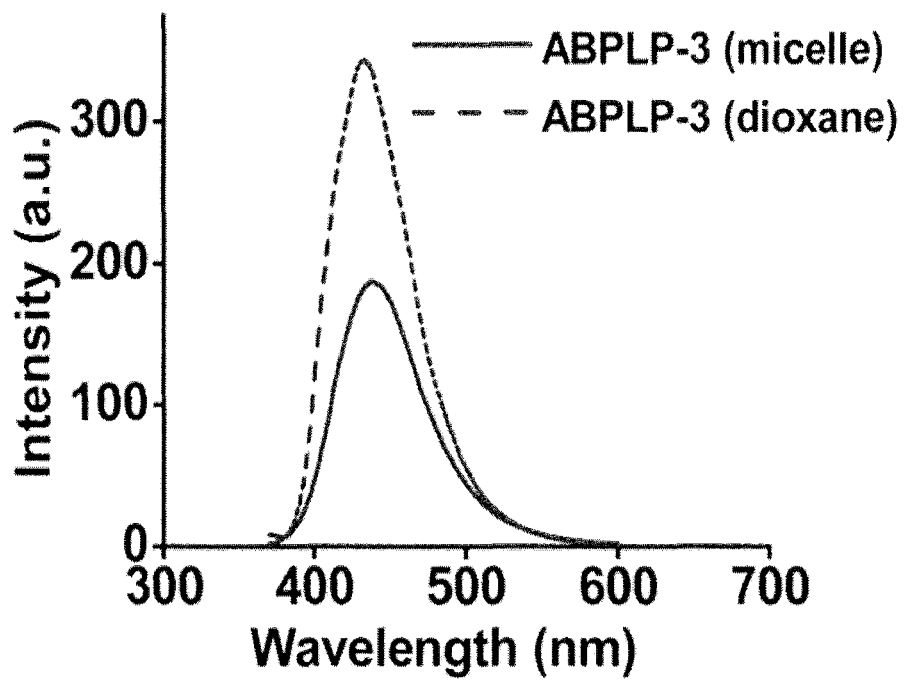
FIG. 13 illustrates optical properties of a micelle and block copolymer according to some embodiments described herein.

Results for one representative ABPLP (ABPLP-Cys, 0.2 molar ratio) were as follows. As compared to the corresponding BPLP-Cys, ABPLP-Cys micelles also showed a strong fluorescence emission in water within the range of 390-550 nm, with a peak wavelength at 446 nm (FIG. 12). However, the quantum yield of ABPLP-Cys was significantly reduced in micelle form when compared to that of BPLP-Cys polymer in 1,4-dioxane when excited at 350 nm (FIG. 13). The same effect was also observed with other ABPLP copolymers (FIG. 11, Table II). For example, the quantum yields of ABPLP-1, ABPLP-2, ABPLP-3, ABPLP-4, and ABPLP-5 were 0.453, 0.443, 0.447, 0.434, and 0.424, respectively, in 1,4-dioxane solution. In micelle form, the quantum yields were significantly reduced to 0.046, 0.072, 0.158, 0.256, and 0.266, respectively (Table II). On the other hand, the molar absorption coefficients (ε) were found to be significantly higher for all ABPLPs in micelle form when compared to the corresponding BPLPs in 1,4-dioxane solution.

TABLE II

Some Properties of Block Copolymers and Micelles.

| Polymer | QY (dioxane solution) | QY (micelle solution) | ε (L·mol$^{-1}$·cm$^{-1}$) (dioxane solution) | ε (L·mol$^{-1}$·cm$^{-1}$) (micelle solution) |
|---|---|---|---|---|
| ABPLP-1 | 0.453 | 0.047 | 514.5 | 5560 |
| ABPLP-2 | 0.443 | 0.072 | 345.9 | 3560 |
| ABPLP-3 | 0.447 | 0.158 | 360 | 2450 |
| ABPLP-4 | 0.434 | 0.256 | 342.4 | 1810 |
| ABPLP-5 | 0.424 | 0.266 | 356.8 | 1740 |

The photostability of ABPLP micelles was also investigated and compared to the organic fluorescent dye rhodamine-B. The fluorescence intensity of the ABPLP micelle solution decreased by only 1 percent of the initial intensity after continuous UV excitation for 3 h, indicating excellent photostability. In contrast, rhodamine-B lost almost 10 percent of initial fluorescence intensity within the same experimental period.

Figure 14:
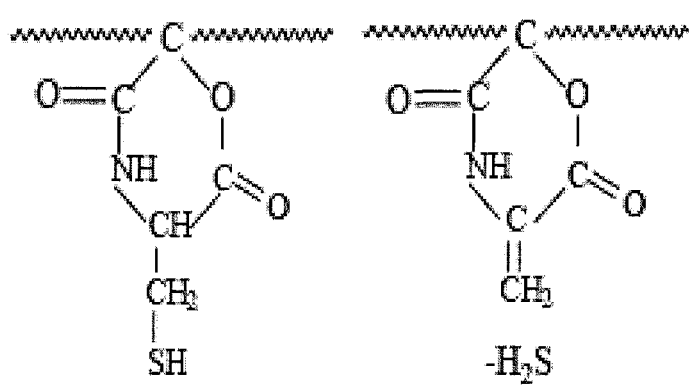
FIG. 14 illustrates the structures of 6-membered rings of a block copolymer according to some embodiments described herein.

Furthermore, a family of ABPLP polymers was synthesized using different alpha-amino acids. For example, ABPLP-Ser, when synthesized with L-serine, exhibited different fluorescence colors ranging from blue to red (emission peaks centered at approximately 415 nm to about 600 nm) by varying the excitation wavelength (from 330 to 582 nm). Not intending to be bound by theory, the excitation-dependent emission of ABPLP-Ser may be due to the Red-Edge Effect (REE), in which polar and rotatable fluorophores embedded in a rigid and highly viscous medium can be observed to generate variable fluorescence emission. It is believed that in the BPLP or ABPLP structures, the polymer backbones can be treated as a viscous medium for the pendant 6-membered ring fluorophores. The R group (—$CH_2OH$) on the 6-membered ring of ABPLP-Ser is highly rotatable and thus may be responsible for the excitation-dependent fluorescence of ABPLP-Ser. In addition, it is also possible that an $H_2S$ elimination occurs during the BPLP-Cys or ABPLP-Cys formation, resulting in a double bond formation to extend the conjugation system of the 6-membered ring (FIG. 14). The double bond may restrict the rotation of the fluorophore, which could explain why ABPLP-Cys does not show excitation-dependent fluorescence.

Figure 15:
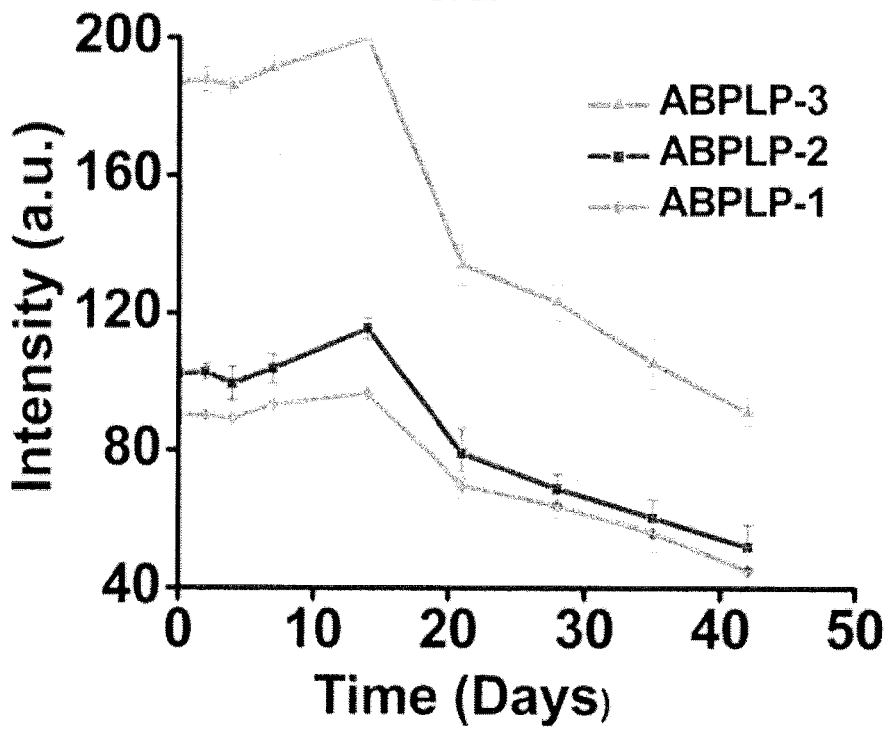
FIG. 15 illustrates optical properties of micelles according to some embodiments described herein.

The long-term fluorescence stability of ABPLP micelles in an aqueous system (phosphate buffered saline, pH 7.4) was monitored for a 6-week period (FIG. 15). In the first week, the fluorescence intensity of the micelles was nearly constant for all micelle systems, followed by an increase in the fluorescence intensity at 2 weeks, and then a continuous decrease thereafter. This result may suggest that ABPLP micelles maintained their thermodynamic stability in the first week and then displayed a higher fluorescence intensity due to dissociation of the polymeric chains after week 2. Not intending to be bound by theory, it is believed that the continuous decrease in fluorescence intensity afterwards was due to the degradation of the BPLP chains of ABPLPs.

EXAMPLE 3

Methods of Imaging and Treating Diseased Tissue

To demonstrate the potential of ABPLP micelles for imaging and/or therapeutic applications, the cellular uptake and fluorescence imaging of the micelles of Example 2 both in vitro and in vivo were examined as follows.

Paclitaxel (PTX) loaded ABPLP micelles were prepared using the solvent evaporation method. In particular, ABPLP (100 mg) polymer in 5 mL of DMF was mixed with 25 mg of PTX (a hydrophobic anti-cancer drug used widely in pharmaceutical research). The mixture was stirred for 2 h in a closed container. 500 µL of the polymer/drug solution was added drop wise under gentle stirring to 20 mL of deionized water. Thereafter, the mixture was dialyzed against deionized water using dialysis tubing molecular weight cut-off 500 Da for 24 h. In order to determine the drug loading (DL) and encapsulation efficiency (EE), drug loaded micelles were centrifuged at 12000 rpm. Then, the PTX in the supernatant was assayed by a SHIMADZU UV-2450 spectrophotometer at a wavelength of 227 nm. The DL was defined as the percentage of PTX to micelle, and EE was defined as the percentage of the actual amount of PTX encapsulated to the original amount of PTX.

After dialysis, in vitro drug release studies were performed in 100 mL phosphate buffer saline (PBS; pH 7.4) as a releasing medium at 37° C. 10 mL of PTX-loaded ABPLP micelles was placed in a dialysis bag (MW cut-off of 500 Da). The dialysis bag was then immersed in the release medium and kept in a horizontal laboratory shaker at a constant temperature (37° C.). In order to measure the drug release content, samples (1 mL) were removed periodically and the fresh PBS replaced an equivalent volume. The amount of released PTX was analyzed with a UV-visible spectrophotometer at 227 nm. Absorbance was measured using a SHIMADZU UV-2450 spectrophotometer. The experiments were performed in triplicate for each of the samples.

The relative cytotoxic effects of ABPLP were evaluated using colorimetric MTS assays (CellTiter 96® $AQ_{ueous}$ One Solution Cell Proliferation Assay, Promega Corp., Madison, Wis.) against NIH-3T3 fibroblasts cells according to the manufacture's protocol. Briefly, 100 µL of 3T3 mouse fibroblasts ($5 \times 10^4$ cells/mL) in DMEM supplemental medium, 10% fetal bovine serum, and 1% of penicillin/streptomycin (100 U/mL penicillin and 100 µg/mL streptomycin) were cultured in a 96-well plate (Costar®, Corning Inc., Corning, N.Y.) for 24 h at 37° C., 5% $CO_2$. The culture medium was then removed and replaced with ABPLP micelles solutions at different concentrations (0-1 mg/mL) in complete DMEM media. After 24 h of incubation, the medium was replaced by 100 µL of fresh media and 20 µL of MTS stock solution. The cultures were incubated for another 4 h, and the absorbance of the dissolved tetrazolium salt solution was measured at 490 nm using a microplate reader. The relative cell viability was calculated by the following equation: relative cell viability (%)=(ODtreated/ODcontrol)×100, where ODcontrol was obtained in the absence of copolymers and ODtreated was obtained in the presence of copolymers. The percentage of relative cell survival to the control (cells exposed to regular culture media) was estimated.

The pharmacological activity of PTX loaded ABPLP micelles was evaluated against PC3 cells using MTS assay as described above. 200 µL of various dilutions of PTX (0.01 to 0.25 mg/mL)-loaded ABPLP-3 micelles were incubated with PC3 cells ($5 \times 10^4$) cultured in a 96-well plate. MTS assay was performed at various time points (4, 12, 24, and 48 h) to understand the pharmacological effect of the drug loaded ABPLP micelles. Drug-free ABPLP-3 (0.5 mg/mL) and 0.25 mg/mL of PTX were used as positive and negative controls, respectively. The percentage of relative cell survival to the control (cells exposed to regular culture media) was estimated.

Amphiphilic block copolymer ABPLP-3 was used to form representative micelles for cellular imaging studies since this copolymer demonstrated the lowest CMC (0.004 mg/mL) compared to other ABPLPs. 3T3 mouse fibroblasts were pre-seeded on sterile glass cover slips at a density of 5,000 cells per mL. After the cells grew to approximately 60% confluency, the cover slip was washed with PBS, transferred to new a petri dish, and incubated with a solution of ABPLP-3 micelles at 0.5 mg/mL. After 3 h incubation at 37° C., the cells were washed by PBS and observed under fluorescence microscope. For longer cell uptake studies (after 3 h of incubation of cell with micelle solution), the micelle solution was replaced with culture media and incubated for the desired duration and observed under fluorescence microscope.

For micelle in vivo bioimaging studies, ABPLP micelle solutions at various concentrations (0.0625 to 1 g/L) were sterilized by filtering through a syringe filter (0.22 µm) and injected into C57BL/6 mice, purchased from Taconic Farms (Germantown, N.Y.). After 30 minutes, the mice were imaged using a Kodak In-Vivo FX Pro system (Carestream Health Inc., New Haven, Conn., USA) with an excitation wavelength of 510 nm and an emission wavelength of 535 nm. The region of interest was drawn after background correction over the injected site, and the mean fluorescence intensities for all pixels in the fluorescence images were calculated using Carestream Molecular Imaging Software, Network Edition 4.5 (Carestream Health). Animals were cared for in compliance with the regulations of the animal care and use committee (IACUC) of The University of Texas at Arlington.

Figure 16:
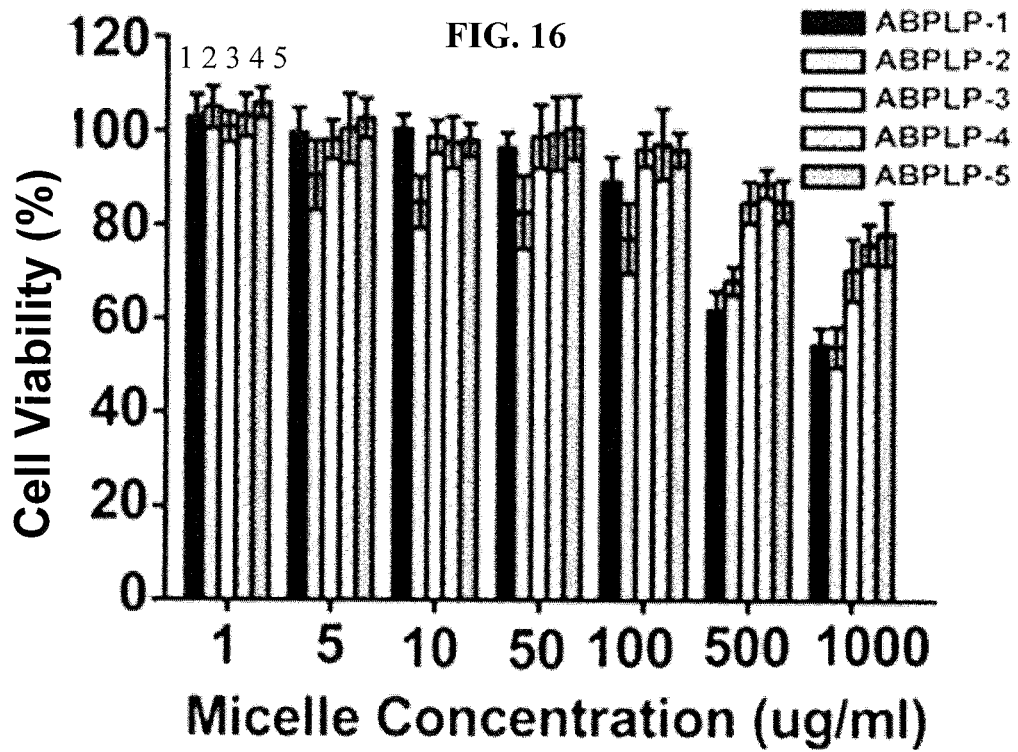
FIG. 16 illustrates cytotoxicity data for micelles according to some embodiments described herein.

The results were as follows. ABPLP micelles were used to label NIH 3T3 fibroblasts with fluorescence colors after 3 h of incubation. The micelles may have only accumulated on the cell surfaces at 3 h, thus the entire cell bodies appeared fluorescent. When cells were imaged at 9 h, cell nuclei were obvious and the cytoplasm was labeled with a blue color, suggesting the micelles were taken up by the cells. When incubated with NIH 3T3 fibroblasts for 24 h, ABPLP micelles did not show significant cytotoxicity to the cells at concentrations ranging from 1 to 1000 µg/mL. It was also noted that ABPLPs with smaller micelle size (as in the case of ABPLP-3, ABPLP-4, and ABPLP-5) were non-cytotoxic even at high concentrations (>500 µg/mL) (FIG. 16).

To verify the potential for in vivo imaging, ABPLP micelle solutions of various concentrations were subcutaneously injected in a mouse through a 27-gauge needle. ABPLP micelles were detected using a non-invasive in vivo imaging system. The signal intensity doubled when the concentration of micelles was increased from 0.0625 mg/mL to 1 mg/mL Upon closer topical observation of the surrounding tissue at the injection sites, the ABPLP micelles did not induce redness or obvious irritation.

Figure 17:
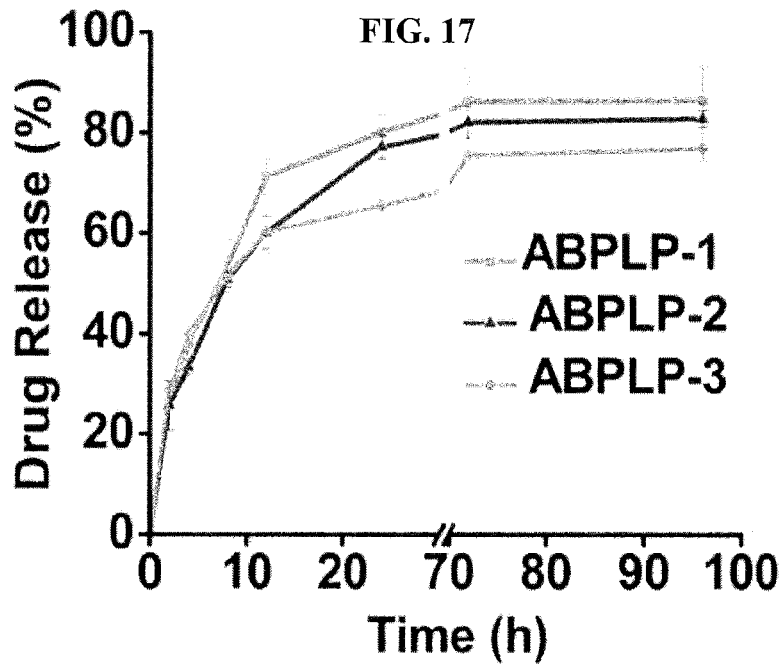
FIG. 17 illustrates drug release properties of micelles according to some embodiments described herein.
Figure 18:
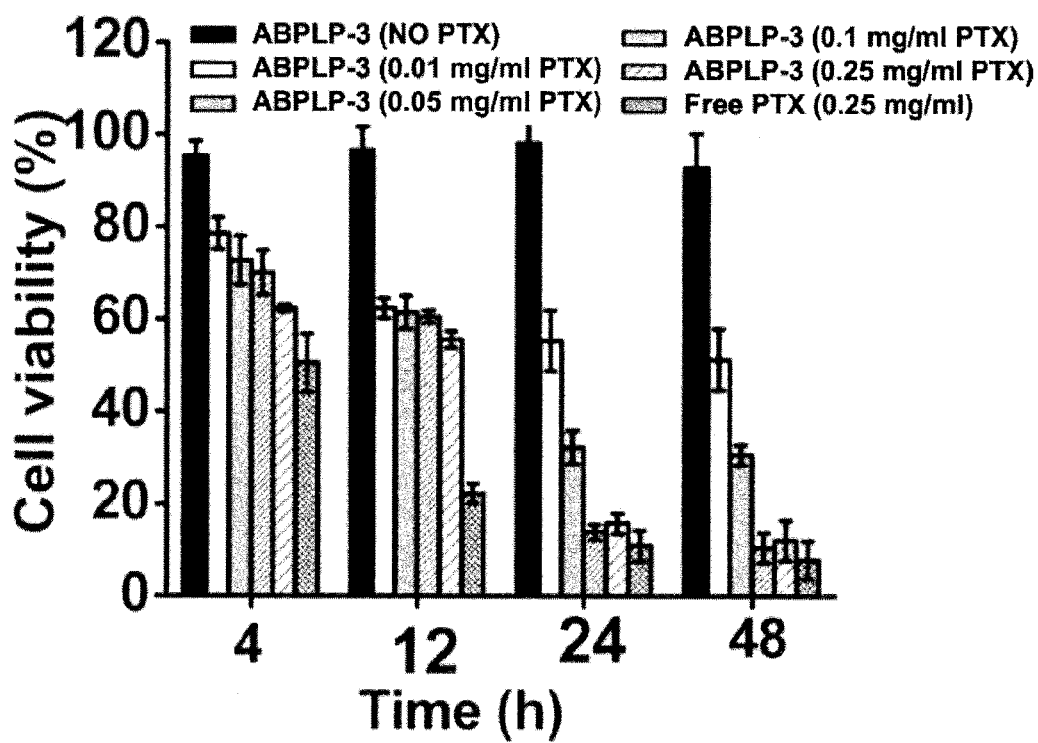
FIG. 18 illustrates pharmacological properties of micelles according to some embodiments described herein.

To demonstrate the utility of ABPLP micelles for cancer drug delivery, Paclitaxel (PTX) was used as a model cancer drug for in vitro drug delivery and cell culture studies. It was observed that all ABPLP micelles have high drug (PTX) loading and encapsulation efficiencies of 20.6 to 22.78% and 81.57 to 91.12%, respectively, as shown in Table III. The PTX release profiles from various ABPLP micelles showed an initial burst release (~50% of the initial loading amount) in the first stage up to 10 h followed by a sustained release period of up to 96 h (FIG. 17). When incubated with a human prostate cancer cell line (PC-3) (FIG. 18), no sign of cellular toxicity was observed for cells incubated with media containing 0.5 mg/mL of drug-free micelles. However, PTX-loaded ABPLP micelles resulted in delayed cell toxicity, with the final toxicity at 24 h comparable to free PTX. Drug free micelles (0.5 mg/mL) and free PTX (0.25 mg/mL) were used as negative and positive controls, respectively. PTX was dissolved in 1% DMSO.

TABLE III

Some Properties of Micelles.

| Polymer | Drug Loading (%) | Drug Encapsulation (%) |
| --- | --- | --- |
| ABPLP-1 | 21.73 | 86.91 |
| ABPLP-2 | 22.36 | 89.43 |
| ABPLP-3 | 22.78 | 91.12 |
| ABPLP-4 | 20.39 | 81.57 |
| ABPLP-5 | 20.6 | 82.40 |

EXAMPLE 4

Block Copolymers

A series of block copolymers according to some embodiments described herein were prepared as described below.

Summary

The block copolymers of the present Example can also be referred to as biodegradable photoluminescent polylactones (BPLPLs). The BPLPLs were formed via a ring-opening polymerization of lactone using BPLPs as initiators. Specifically, terminal hydroxyl groups of BPLPs permitted the ring-opening polymerization of monomers like lactide to make completely degradable tri-block copolymers. In this Example, poly(L-lactide)-co-BPLP (BPLP-PLAs or BPLP-PLLAs) are described. However, a family of similar BPLP copolymers with poly(D,L-lactide), polyglycolide, and poly(ε-caprolactone) were also synthesized in a similar manner. The resulting BPLPL copolymers possessed similar physical and thermal properties as polylactones while providing tunable intrinsic fluorescence. The BPLPLs can further be described using the following nomenclature: BPLP-[amino acid]-[lactide][molar ratio of lactide to BPLP]. For example, the nomenclature "BPLP-Cys-PLA20" or "BPLP-Cys-PLLA20" refers to a block copolymer formed from a BPLP formed using cysteine as the amino acid and L-lactide as the lactide monomer, where the molar ratio of lactide to BPLP in the starting materials was 20:1. The BPLP:lactide molar ratios used in this Example were 1:20, 1:50, and 1:100. In addition, by using polyethylene glycol (PEG) as the diol of the starting material BPLP, water-soluble BPLPs (WBPLP) were made. After copolymerization with PLA, amphiphilic biodegradable photoluminescent WBPLP-PLAs were prepared. BPLPLs described herein can be applied as medical implants or scaffolds that can be tracked non-invasively by fluorescence imaging and also as label-free imaging probes/drug delivery devices for targeted theranostic applications.

Materials and Methods

Synthesis of BPLPLs.

BPLP prepolymers with terminal hydroxyl groups were synthesized first with citric acid and diol in a molar ratio of 1:1.1 as described above in Example 1. L-Cysteine and L-Serine were selected to synthesize BPLP-Cys and BPLP-Ser. Polyethylene glycol ($M_n$=200) was used to prepare water-soluble BPLPs (WBPLPs). BPLPLs were synthesized via enzyme catalyzed ring-opening polymerization using pre-BPLP as macro-initiators. Typically, freeze-dried BPLP was added into a dry 100 mL flask, and then lactones (for example, L-lactide) (purified twice by recrystallization) were added into the flask with different ratios to BPLP. Next, porcine pancreas lipase (PPL, dried overnight under vacuum) was added into the flask with a ratio of 5% to lactone. The flask was evacuated by vacuum and purged with nitrogen three times, then sealed and heated to 100° C. and held at that temperature for 72 hrs. The copolymer was dissolved in chloroform and PPL was removed by filtration through a fritted filter. The polymer solution was concentrated under reduced pressure and then precipitated in cold methanol. When WBPLP was used to synthesize an amphiphilic copolymer, the product was dissolved by dimethyl sulfoxide (DMSO) and precipitated in cold deionized (DI) water after filtration.

Preparation of Films, Nanoparticles, Micelles and Nanofibers.

BPLP-PLA films were prepared by casting a chloroform solution of BPLP-PLA into Teflon molds, followed by evaporation of the chloroform. BPLP-PLA nanoparticles were prepared using a nanoprecipitation technique. Specifically, 5 mg of BPLP-PLA polymer was dissolved in 5 mL of THF. The polymeric solution was added dropwise to 50 mL of deionized water. The solution was stirred at a speed of 700 rpm and the solvent was allowed to completely evaporate at room temperature. WBPLP-PLA micelles were fabricated in a similar manner. Fluorescent BPLP-PLA nanofibers were fabricated by electrospinning 12% wt BPLP-Ser-PLA50 chloroform solution at 18 kV and 2.5 µL/min onto an aluminum board.

Polymer Characterization.

FTIR spectra were collected at room temperature. To prepare the FTIR samples, BPLP-PLA copolymer was dissolved in chloroform and cast onto KBr pellets. The solvent was allowed to evaporate overnight in a chemical fume hood. FTIR spectra were collected using a Nicolet 6700 FT-IR spectrometer (Thermo Fisher Scientific) at room temperature. For $^1$H NMR measurements, 10 mg of copolymer was dissolved in 1 mL of deuterated chloroform or DMSO. The NMR spectra were collected on a JEOL 500 MHz spectrometer at room temperature. Gel permeation chromatography (GPC) was used to determine molecular weights as follows. Copolymer was dissolved in chloroform and analyzed using a Shimadzu high performance liquid chromatography (HPLC) system equipped with a Phenomenex Phenogel 5µ 10E3 SEC column, a Wyatt miniDAWN light scattering detector, and an OptiLab RI detector.

Photoluminescence Properties.

UV-vis absorption spectra were collected using a Shimadzu UV-2450 spectrophotometer. A dilute solution of copolymer was prepared in DMSO. All photoluminescence spectra were obtained using a Shimadzu RF-5301PC fluorospectrophotometer. Both the excitation and the emission slit width were set at 1.5 nm for all samples unless otherwise stated. Quantum yields of all samples were determined by the method of Williams et al., *Analyst* 1983, 108, 1067. Anthracene (quantum yield=0.27 in ethanol) was used as the standard.

Thermal Properties.

Thermal analysis was conducted on a differential scanning calorimeter (DSC, TA Instrument Q2000) at a ramp rate of 10° C./min. A TA instrument TGA Q500 thermogravimetric analyzer was used to measure the thermal degradation of the copolymers at a ramp rate of 10° C./min from 0° C. to 500° C.

In Vitro Degradation.

In vitro degradation of BPLP-PLA copolymer was carried out by placing 50 mg of copolymer in a tube containing 10 mL of phosphate buffer saline (PBS) (pH=7.4). All copolymer samples were incubated at 37° C. for predetermined time points. After the predetermined incubation period, the samples were taken out and washed with water and lyophilized. The degradation was characterized based on the mass of copolymer remaining. The in vitro degradation was also monitored by fluorescence loss.

Cell Culture and In Vitro Studies.

Polymer cytocompatibility was evaluated in vitro using NIH 3T3 fibroblast cells, which were cultured in 75 cm$^2$ tissue culture flasks with Dulbecco's modified eagle's medium (DMEM) supplemented with 10% fetal bovine serum (FBS) and 1% antibiotics. The cells were trypsinized, centrifuged, and suspended in media to obtain a seeding density of $5 \times 10^5$ cell/mL. 200 µL of the suspension was added into 96-well plates. The cells were then incubated at 37° C., 5% $CO_2$ and 95% humidity for 24 hours. Next, nanoparticles of BPLP-PLA copolymers or control polymers (BPLP polymers or poly(L-lactide) (PLLA) polymers) were added at various concentrations. MTT assay was used to assess the viability of the cells after 4 hr and 24 hr. The data obtained was normalized to the viability of cells cultured on tissue culture plate.

Cell Uptake and Fluorescence Labeling.

The cell uptake of the fluorescent nanoparticles was also examined in vitro. 3T3 fibroblasts were seeded onto sterile cover slips with a seeding density of 5,000 cells/mL. Cells were allowed to attach and grow for 24 hours before uptake studies were performed. The cover slips were washed with PBS and transferred into a Petri dish. After 4 hours of incubation with BPLP-Ser-PLA50 nanoparticles (100 µg/mL), the media was aspirated and the cells were washed three times with PBS to remove the excess nanoparticles, which had not been taken up. The cells were fixed with 2.5% glutaraldehyde for 2 hours. After fixing, the cover slips were mounted on glass slides and imaged under a Leica DMLP fluorescence microscope (Leica Microsystems, Bannockburn, Ill.) equipped with a Nikon E500 Camera (8.4V, 0.9A, Nikon Corp., Japan).

In Vivo Degradation.

To measure the in vivo degradation, a disk of BPLP-Ser-PLA20 having a diameter of 8 mm and a thickness of 1 mm was implanted subcutaneously in a 6 week old nude mouse (32 nude mice were used in total). At each designed time point, the animals were imaged by a Maestro™ in vivo fluorescent imaging system (Caliper Lifer, Mountain View, Calif.) with a 580 nm excitation light source. The fluorescence intensity was calculated after eliminating the autofluorescence signal. After implantation periods of 2, 4, 6, 8, 10, 12, and 16 weeks, four mice were sacrificed to measure the weight loss of BPLP-Ser-PLA20 disks. All samples were carefully removed from surrounding tissue, washed by PBS, lyophilized and weighed.

In Vivo Biocompatibility Evaluation.

For evaluation of the in vivo host response, films of BPLP-PLA copolymers were placed subcutaneously in 1-year-old male Sprague Dawley rats (Harlan Sprague Dawley, Inc., Indianapolis, Ind.) under deep isoflurane-$O_2$ general anesthesia. All the animals were observed daily for any change in their behavior over the period of the experiment. At each pre-determined time point (7 days and 60 days), three animals were sacrificed with excess $CO_2$, and polymers with surrounding tissues were harvested for further evaluation. The explants were fixed by soaking in 10% formalin for 2 days. The samples were processed on an automated tissue processor, embedded in paraffin wax, and sectioned into 4 µm sections. Six slides from different areas of the explants were stained with hematoxylin and eosin staining. The cross-sections were examined using a Leica DMLP microscope (Leica Microsystems Inc., Bannockburn, Ill.) fitted with a Nikon E500 camera (Nikon Corp., Japan).

Tumor Targeted Imaging.

For in vivo tumor targeting and imaging tests, a subcutaneous breast cancer model was used. Specifically, $1 \times 10^5$ MCF7 cells were injected on the back of a 6 week old nude mouse. BPLP-Ser-PLA50 nanoparticles were conjugated with folate by EDC/NHS chemistry before injecting the nanoparticles intravenously via tail vein at a concentration of 5 mg/mL and a volume of 200 µL. After 4 and 6 hours post-injection, the animals were imaged by a Maestro™ in vivo fluorescent imaging system as described above. The animals were sacrificed after 8 hours, and all organs were removed to study the biodistribution via fluorescence imaging.

Results

Table IV provides the properties of various BPLPLs prepared as described above. $^1$H-NMR and FTIR confirmed that the chemical structure of BPLP-PLAs contained functional groups of both BPLPs and PLAs. In Table IV below, "BPLP:LA" refers to the molar feeding ratio of BPLP to lactide; "CA:LA" refers to the molar ratio of citric acid to lactide in the BPLP (as determined by $^1$H-NMR); "$M_W$ (NMR)" is the weight average molecular weight in Daltons as estimated from $^1$H-NMR based on a molecular weight of 1300 Da for the BPLP initiator, as determined by MALDI-MS; "$M_W$ (GPC)" is the weight average molecular weight in Daltons as determined by gel permeation chromatography (GPC); "yield" is the % reaction yield, determined as the ratio of the weight of the resulting polymer to the total weight of the monomers used to form the polymer; and "QY" is the % quantum yield.

Figure 19:
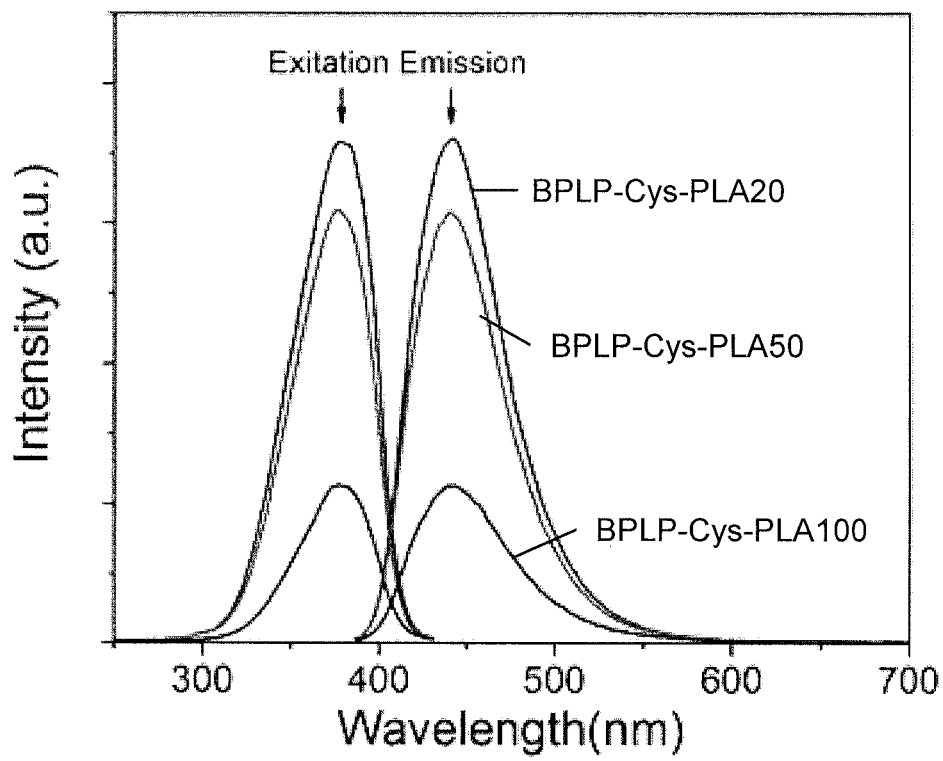
FIG. 19 and FIG. 20 each illustrates optical properties of block copolymers according to some embodiments described herein.
Figure 20:
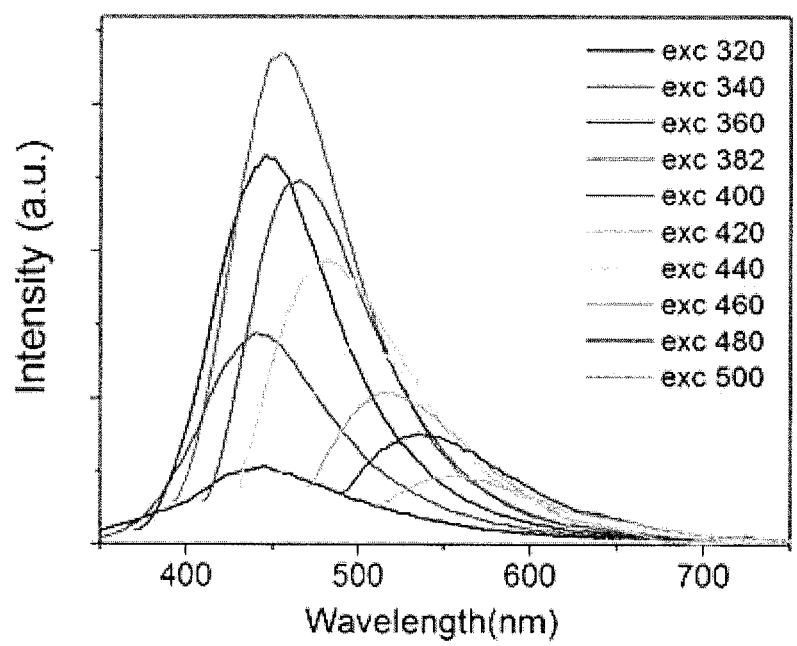

All BPLP-PLA copolymers emitted strong fluorescence, as shown in FIG. 19 and FIG. 20. For BPLP-Cys-PLA, the maximum emission (441 nm) and excitation (377 nm) is slightly different than the BPLP-Cys pre-polymer. At the same concentration (10 mg/mL), copolymers having longer PLA blocks exhibited a decreased fluorescence intensity (FIG. 19). BPLP-Ser-PLA exhibited tunable fluorescence, with the fluorescence emission depending on the excitation wavelength. As shown in FIG. 20, BPLP-Ser-PLA50 displayed fluorescence emission peaks from 350 nm to 700 nm. In addition, BPLP-Cys-PLA copolymers exhibited quantum yields up to 51% (Table IV).

TABLE IV

Some Properties of Block Copolymers.

| Copolymer | BPLP:LA | CA:LA | $M_W$ (NMR) | $M_W$ (GPC) | Yield | QY |
|---|---|---|---|---|---|---|
| BPLP-Cys-PLLA20 | 1:20 | 1:8.76 | 3823 | 5319 | 48 | 39.9 |
| BPLP-Cys-PLLA50 | 1:50 | 1:22.05 | 7650 | 10274 | 46 | 51.4 |
| BPLP-Cys-PLLA100 | 1:100 | 1:31.21 | 10288 | 12369 | 33 | 13.5 |
| BPLP-Ser-PLLA20 | 1:20 | 1:8.77 | 3826 | 5971 | 77 | 9.3 |
| BPLP-Ser-PLLA50 | 1:50 | 1:19.04 | 6784 | 7894 | 43 | 4.9 |
| BPLP-Ser-PLLA100 | 1:100 | 1:32.73 | 10726 | 14257 | 38 | 1.5 |
| WBPLP-Cys-PLLA20 | 1:20 | 1:5.34 | 2838 | — | 39 | 27.4 |
| WBPLP-Cys-PLLA50 | 1:50 | 1:7.38 | 3425 | — | 27 | 21.1 |
| WBPLP-Cys-PLLA100 | 1:100 | 1:9.09 | 3918 | — | 35 | 15.4 |

Figure 21:
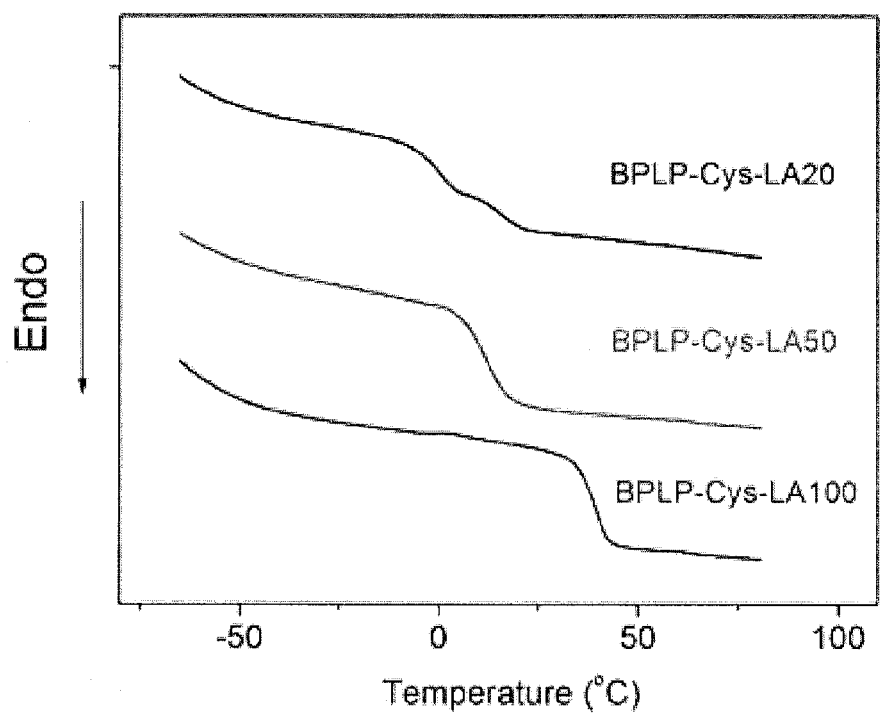
FIG. 21 and FIG. 22 each illustrates thermal properties of block copolymers according to some embodiments described herein.
Figure 22:
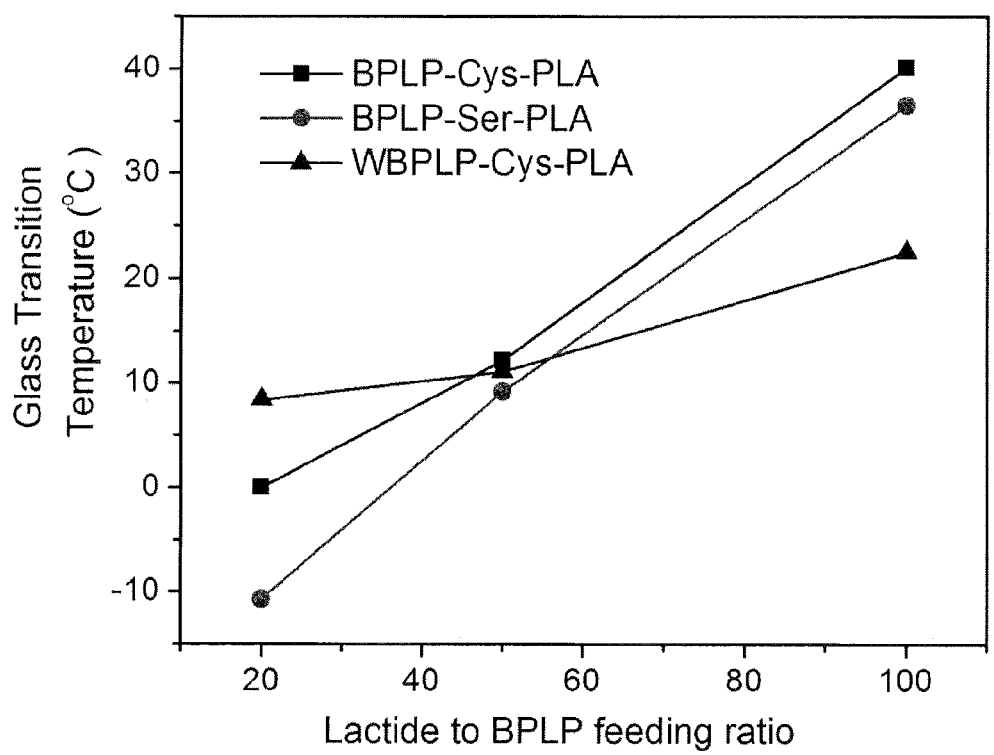

BPLP-PLAs were plastic-like and thermally stable. FIG. 21 illustrates DSC thermograms of BPLP-Cys-PLA copolymers with different molecular weights. The glass transition temperature (Tg) increased gradually with longer PLA blocks. For BPLP-Cys-PLA100, the Tg was higher than 40° C. The same trend was also exhibited by BPLP-Ser-PLA and WBPLP-PLA, as shown in FIG. 22. When thermally decomposed, BPLP-Cys-PLA20 exhibited a slight weight loss at 120° C., possibly due to the crosslinking of BPLP. However, no weight loss was observed before 280° C. for BPLP-Cys-PLA100.

Figure 23:
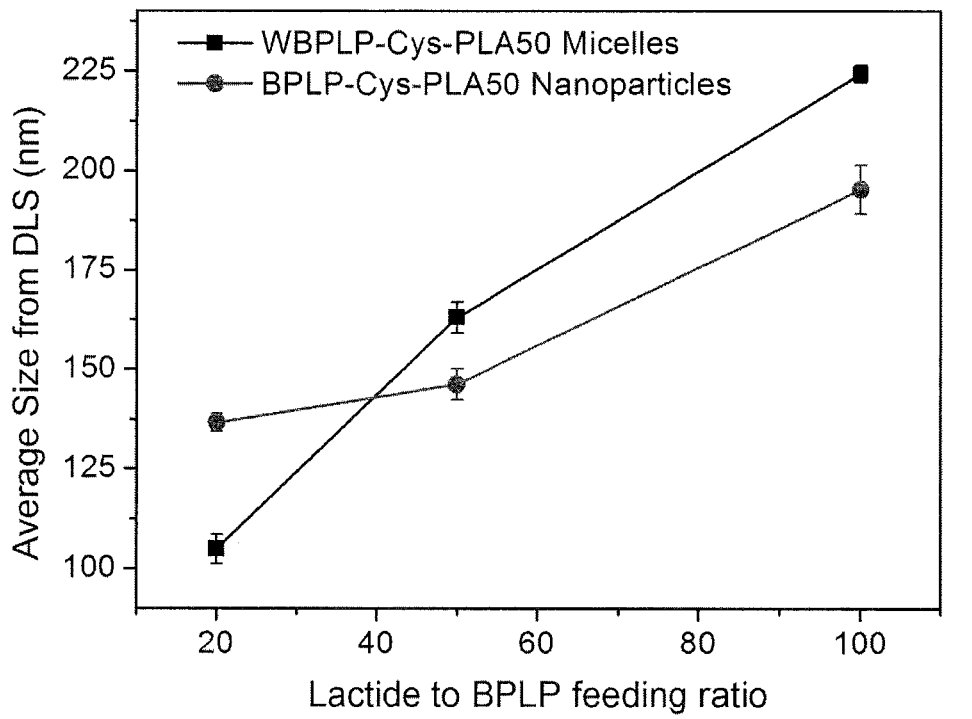
FIG. 23 illustrates the sizes of secondary structures of block copolymers according to some embodiments described herein.
Figure 24:
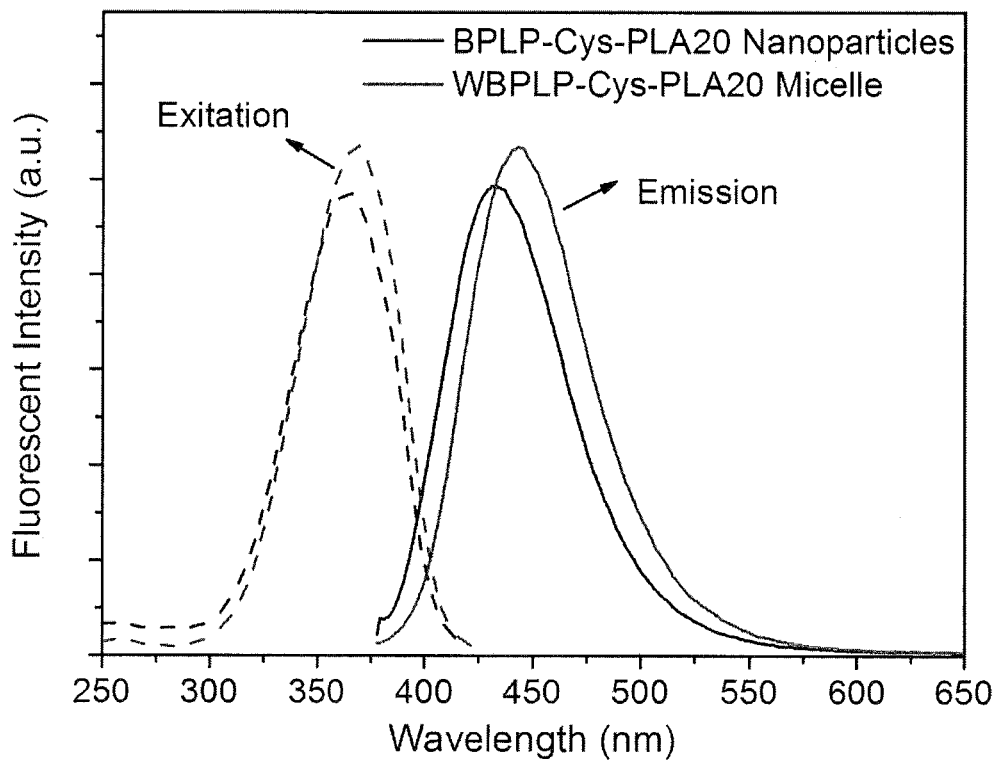
FIG. 24 illustrates optical properties of secondary structures of block copolymers according to some embodiments described herein.

BPLP-PLA nanoparticle sizes, micelle sizes, and drug delivery profiles could also be tuned based on the amount of lactide used, as shown in FIG. 23. In addition, the CMC of amphiphilic WBPLP-PLA micelles could be varied. For example, the CMCs for WBPLP-Cys-PLA20 and WBPLP-Cys-PLA50 were $1.283 \times 10^{-2}$ g/L and $7.262 \times 10^{-3}$ g/L, respectively. Further, both nanoparticles and micelles of block copolymers described herein exhibited strong fluorescence in solution, as shown in FIG. 24. Moreover, BPLP-Ser-PLA50 nanoparticles were taken up by 3T3 fibroblast in vitro and imaged by fluorescent microscopy, thus verifying the imaging label capability of these probes. Additionally, BPLP-PLA nanoparticles exhibited similar in vitro cytocompatibility relative to PLLA, as shown in FIG. 25 and FIG. 26. BPLP-Ser-PLA50 polymers were also electrospun into uniform ultra-fine fibers that exhibited strong photoluminescence under microscopy.

Figure 27:
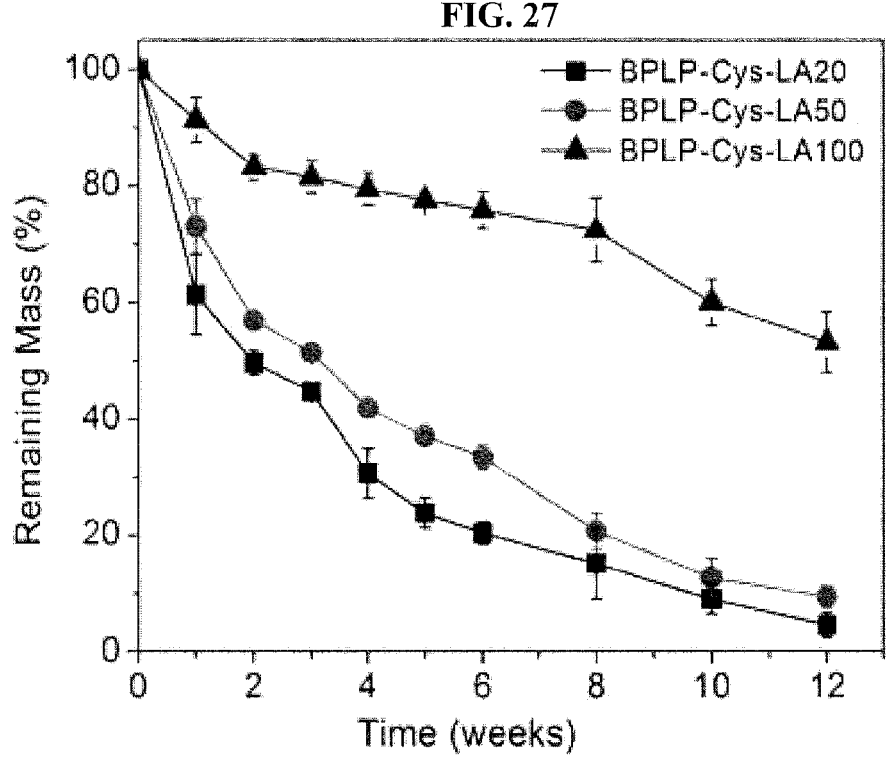
FIGS. 27 through 29 illustrate in vitro and in vivo degradation properties of block copolymers according to some embodiments described herein.
Figure 28:
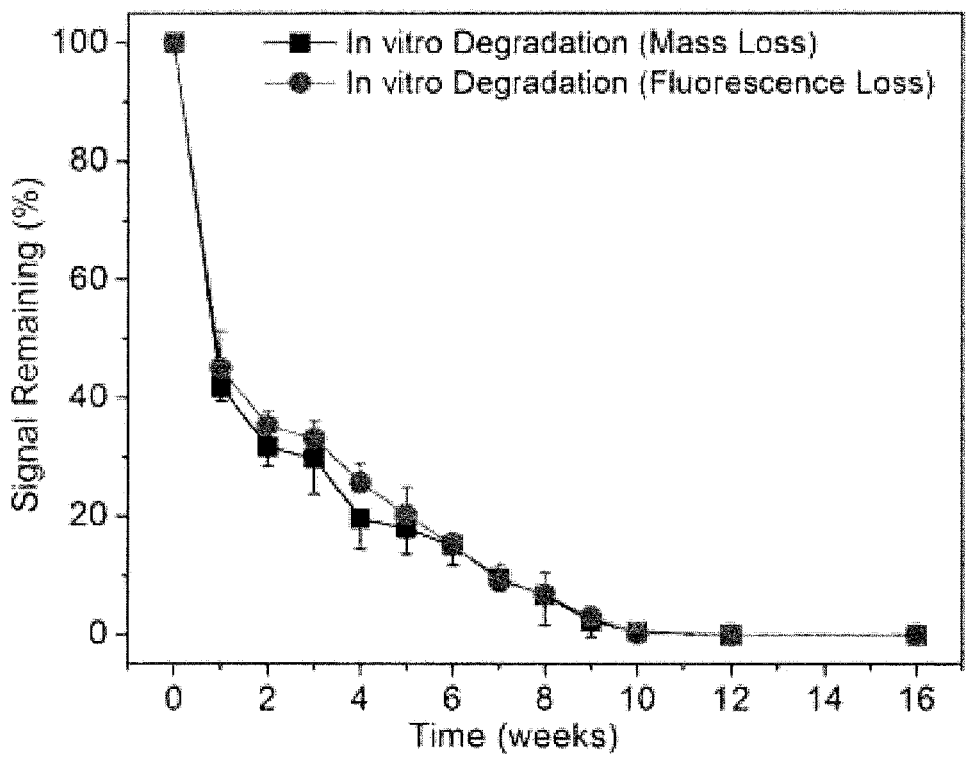
Figure 29:
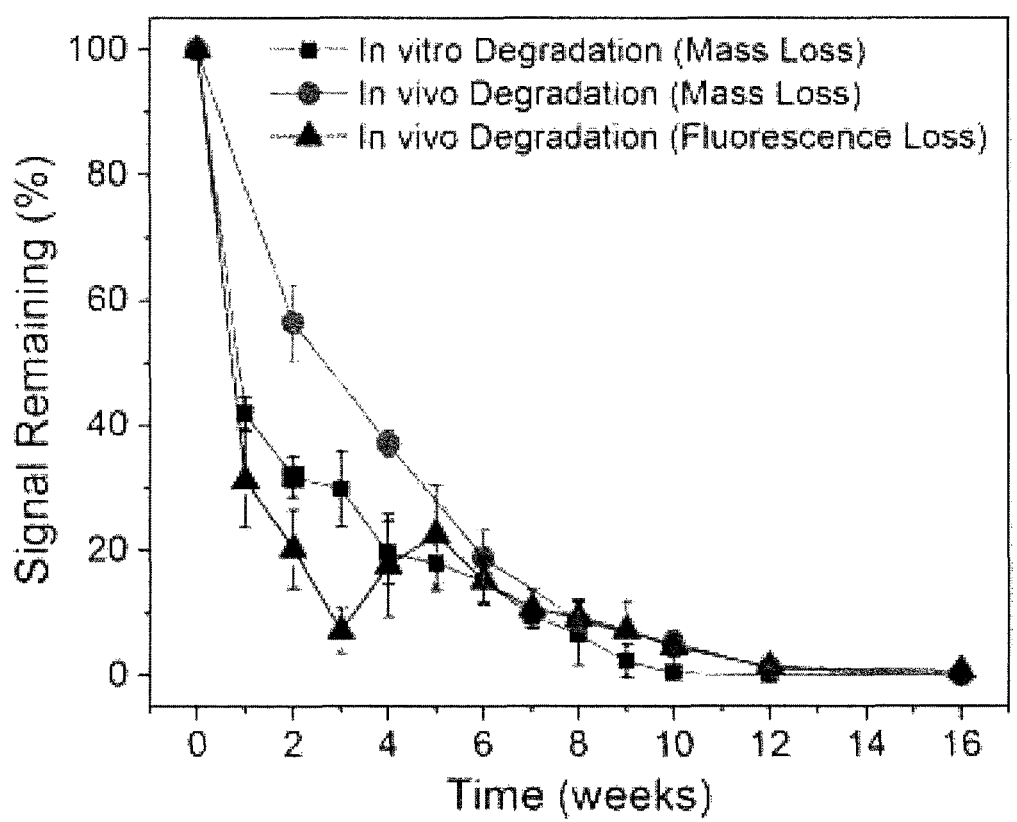

The in vitro weight loss rate of BPLP-PLAs was dependent on the length of PLA blocks (FIG. 27). BPLP-Cys-PLA20 completely degraded after 12 weeks of incubation in PBS, while the degradation rate of BPLP-Cys-PLA100 was almost the same as PLLA. As described above, the degradation of BPLP-PLAs could also be measured by fluorescence signal decay, instead of or in addition to by weight loss (FIG. 28). As shown in FIG. 29, the weight of BPLP-Ser-PLA20 decreased faster in PBS than in vivo when subcutaneously implanted in nude mice.

To access in vivo biocompatibility, films of BPLP-Ser-PLA20 copolymers were placed subcutaneously in 1-year-old male Sprague Dawley rats. PLLA and cross-linked BPLPs were chosen as controls. Histological analysis showed the presence of inflammatory cells at both 1 and 10 weeks implantation. After 1 week of implantation, the acute inflammatory response was mild for all samples. BPLP-Ser-PLA20 elicited a slightly thicker layer of surrounding fibrous capsules compared to PLLA and cross-linked BPLP. However, no significant difference was observed between PLLA, CBPLP films and BPLP-Ser-PLA20 in the aspect of cell density and capsule layer thickness. After 1 week of implantation, CD11b+ cell were also observed around the implanted materials. The immunohistochemical analysis indicated that almost the same amount of CD11b+ inflammatory cells infiltrated into CBPLP and BPLP-Ser-PLA20 implants as for PLLA. The assessment of chronic inflammatory response at 10 weeks revealed thicker fibrous capsules for all implants, while BPLP-Ser-PLA20 showed slightly thinner capsule layers and less cell density with no significant difference compared to PLLA.

To demonstrate the feasibility of targeted molecular imaging with full degradation, folates were conjugated onto BPLP-Ser-PLA50 nanoparticles as a targeting ligand. After intravenous injection through the tail vain, the nanoparticles accumulated at the tumor site of a nude mouse breast cancer mode, as detected by fluorescence imaging. Ex vivo fluorescence imaging also confirmed that most of the nanoparticles were located at the tumor, with only a few up-taken by the liver.

EXAMPLE 5

Block Copolymers

A series of block copolymers according to some embodiments described herein were prepared as follows. Specifically, BPLPLs were prepared as described in Example 4 above. In the present Example, the BPLP block/pre-polymer was formed from citric acid, 1,8-octanediol, and L-cysteine (molar ratios of 1:1.1:0.2). The BPLPLs comprised BPLP-co-PLGA copolymers formed via a ring-opening polymerization of D,L-lactide and glycolide using stannous 2-ethylhexanoate as a catalyst. Briefly, various molar ratios of D,L-lactide and glycolide were added to an oven-dried reaction tube with different amounts of BPLP. Then 0.1% by weight (based on the total weight of the mixture of BPLP, D,L-lactide, and glycolide) tin catalyst was added as a solution in dry dichloromethane. The dichloromethane was evaporated under vacuum over 1 h. The tube was then placed under vacuum by three cycles of purging and evacuation. The tube was sealed under vacuum and immersed in an oil bath at 160° C. for 48 h. After 48 h, the reaction product was cooled to ambient temperature. The solid reaction product was dissolved in chloroform and precipitated several times with an excess of pure ethanol to remove unreacted starting materials. BPLP-co-PLGA copolymer was then recovered by vacuum filtration and dried under vacuum at room temperature. The molar ratios of D,L-lactide and glycolide were 75:25 and 50:50 for different copolymers. The ratio of BPLP to the total of D,L-lactide and glycolide was 1:50, 1:100, or 1:200 for different copolymers. The nomenclature "BPLP-co-PLGA50/50 100" represents a copolymer that was synthesized from a feeding molar ratio of D,L-lactide to glycolide of 50:50 and of BPLP to lactides of 1:100.

Figure 30:
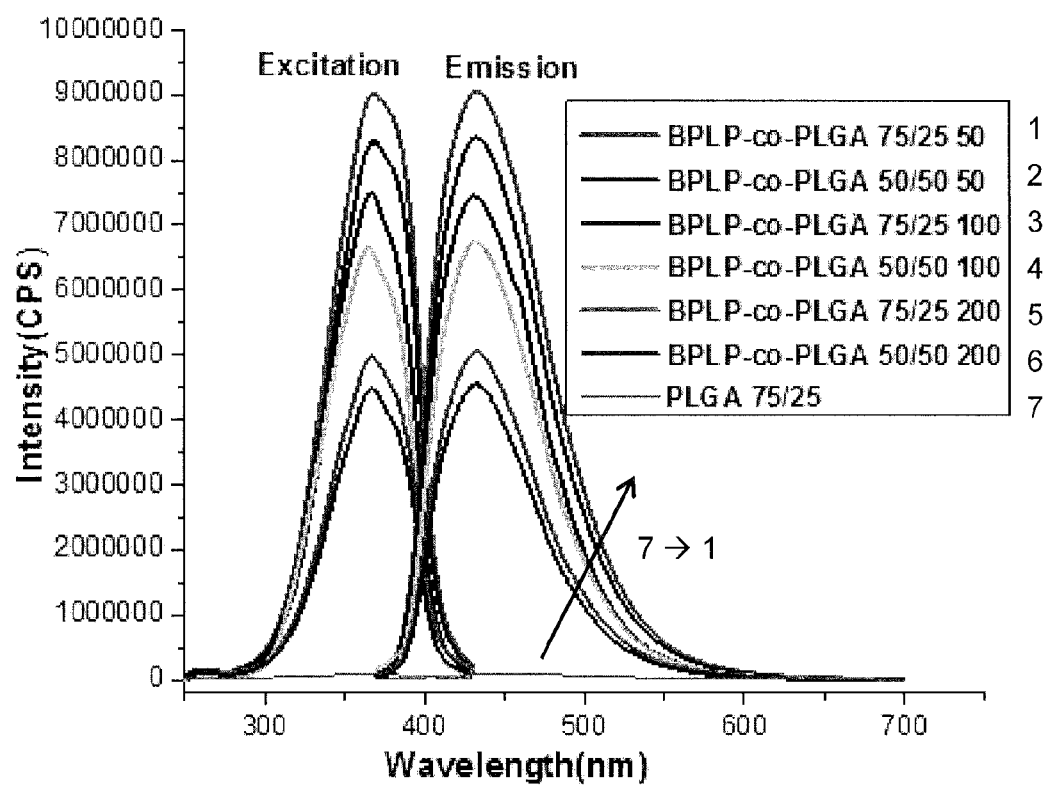
FIG. 30 illustrates fluorescence properties of block copolymers according to some embodiments described herein.
Figure 31:
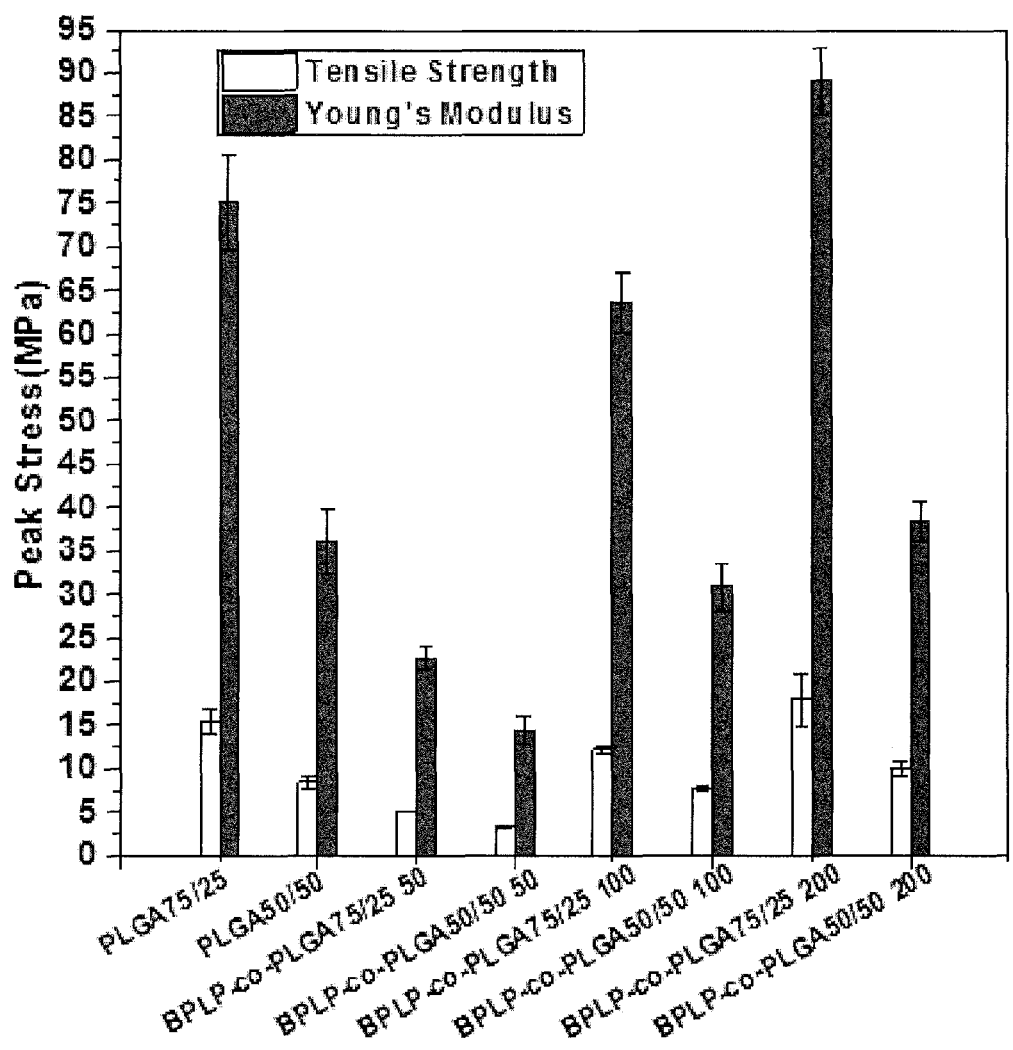
FIG. 31 illustrates mechanical properties of block copolymers and secondary structures of block copolymers according to some embodiments described herein.

FIG. 30 illustrates the fluorescence emission for a series of BPLP-co-PLGAs described above. FIG. 31 illustrates mechanical properties of a series of BPLP-co-PLGAs and BPLP-co-PLGA films described above.

Nanoparticles of BPLP-co-PLGAs were prepared using an emulsion-evaporation technique. Specifically, BPLP-co-PLGA 75/25 100 copolymer was dispersed in chloroform. The chloroform solution was then added to a solution of polyvinyl alcohol (PVA) in water, followed by treatment with ultrasound. This procedure provided nanoparticles of BPLP-co-PLGA stabilized with a PVA shell. The resulting emulsion was stirred mechanically to allow the chloroform to evaporate and to remove the PVA shell from the BPLP-co-PLGA nanoparticles. The BPLP-co-PLGAs were then further purified and lyophilized. The substantially spherical nanoparticles had an average diameter of 180.9 nm. In addition, the nanoparticles exhibited fluorescence in water and uptake by hSMC at a concentration of 1 mg/mL.

EXAMPLE 6

Scaffolds of Block Copolymers

A scaffold of a block copolymer according to one embodiment described herein is prepared as follows. A BPLPL block copolymer is prepared as described above and dispersed in a solvent such as 1,4-dioxane. Salt particles are also prepared by grinding and sieving salt (NaCl) crystals into different size fractions (50-1000 μm). The salt particles are then added to the block copolymer dispersions in various concentrations (5-50 wt.-%) to provide a porous scaffold. Specifically, the slurry of salt and copolymer can be stirred until most of the solvent is removed, resulting in a homogenous viscous paste. The paste can then be added to a mold, such as a cylindrical Teflon mold having a desired inner diameter. Following solvent evaporation, the scaffold can be thermally post-polymerized or crosslinked in an oven, such as an oven maintained at 80-100° C. for 1-3 days. Salt can then be leached out by immersing the scaffold in distilled water.

Various embodiments of the present invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

That which is claimed is:

1. A micelle formed from an amphiphilic polymer, the amphiphilic polymer comprising:
   at least one hydrophilic block comprising a hydrophilic polymer or oligomer; and
   at least one hydrophobic block comprising a hydrophobic polymer or oligomer,
   wherein the hydrophilic polymer or oligomer and/or the hydrophobic polymer or oligomer is formed from the reaction product of (i) a polycarboxylic acid or a polycarboxylic acid equivalent, (ii) a polyol, and (iii) an amino acid, and
   wherein the hydrophilic block and the hydrophobic block are bonded together through an ester linkage;
   wherein the micelle has a hydrophobic core and a hydrophilic corona; and
   wherein a drug is disposed in the hydrophobic core of the micelle.

2. The micelle of claim 1, wherein the micelle is a fluorescent micelle.

3. A medical device formed at least in part from the micelle of claim 1.

* * * * *